US010697961B2

(12) United States Patent
Lockton et al.

(10) Patent No.: US 10,697,961 B2
(45) Date of Patent: Jun. 30, 2020

(54) METHODS FOR PREDICTING POST-OPERATIVE RECURRENCE OF CROHN'S DISEASE

(71) Applicants: Prometheus Biosciences, Inc., San Diego, CA (US); KATHOLIEKE UNIVERSITEIT LEUVEN, Leuven (BE)

(72) Inventors: Steven Lockton, San Diego, CA (US); Marc Ferrante, Leuven (BE); Severine Vermiere, Leuven (BE); Sharat Singh, Rancho Santa Fe, CA (US)

(73) Assignees: Prometheus Biosciences, Inc., San Diego, CA (US); Katholieke Universiteit Leuven, Leuven (BE)

( * ) Notice: Subject to any disclaimer, the term of this patent is extended or adjusted under 35 U.S.C. 154(b) by 340 days.

(21) Appl. No.: 15/161,024

(22) Filed: May 20, 2016

(65) Prior Publication Data

US 2016/0334401 A1 Nov. 17, 2016

Related U.S. Application Data

(63) Continuation of application No. PCT/IB2014/066532, filed on Dec. 2, 2014.

(60) Provisional application No. 61/911,410, filed on Dec. 3, 2013.

(51) Int. Cl.
*G01N 31/00* (2006.01)
*G01N 33/53* (2006.01)
*G01N 33/564* (2006.01)

(52) U.S. Cl.
CPC ..... *G01N 33/564* (2013.01); *G01N 2800/065* (2013.01); *G01N 2800/54* (2013.01)

(58) Field of Classification Search
None
See application file for complete search history.

(56) References Cited

U.S. PATENT DOCUMENTS

| | | |
|---|---|---|
| 2010/0015156 A1 | 1/2010 | Dubinsky |
| 2010/0129838 A1 | 5/2010 | Barken |
| 2011/0045476 A1 | 2/2011 | Barken |
| 2013/0197028 A1 | 8/2013 | Li |

FOREIGN PATENT DOCUMENTS

| | | |
|---|---|---|
| WO | 2008/109782 A2 | 9/2008 |
| WO | 2010/056682 A2 | 5/2010 |
| WO | 2010/120814 A1 | 10/2010 |
| WO | 2011/163539 A2 | 12/2011 |

OTHER PUBLICATIONS

Schoepfer et al. (Inflamm Bowel Dis. Sep. 2009, vol. 15, No. 9, pp. 1358-1367).*
Ajlouni et al. (J Med J, 2009, vol. 43., No. 3, pp. 212-230).*
Lichtenstein (Gastroenterology & Hepatology, Feb. 2010, vol. 6, No. 2, pp. 99-107).*
Tamboli etal. (Clinical and Experimental Gastroenterology, 2011, vol. 4, pp. 127-140).*
Tascilar et al. (Annals of Oncology 10.Suppl. 4:S107-S110, 1999).*
Tockman etal. (Cancer Research 52:2711s-2718s, 1992).*
Fleshner; Both Preoperative Perinuclear Antineutrophil Cytoplasmic Antibody and Anti-CBir1 Expression in Ulcerative Colitis Patients Influence Pouchitis Development After Ileal Pouch-Anal Anastomosis; Clinical Gastroenterology and Hepatology 2008; 6:561-568.
Su; Are there predictors of Remicade treatment success or failure?; Advanced Drug Delivery Reviews; 57 (2005) 237-245.
International Search Authority—International Search Report of PCT/IB2014/066532, dated Mar. 26, 2015.
International Search Report for PCT/IB2014/066532, dated Mar. 26, 2015, 5 pages.
Fleshner, P. et al., "Both Preoperative Perinuclear Antineutrophil Cytoplasmic Antibody and Anti-CBir1 Expression in Ulcerative Colitis Patients Influence Pouchitis Development After Ileal Pouch-Anal Anastomosis," Clinical Gastroenterology and Hepatology, American Gastroenterological Association, 6(5):561-568, 2008.
Su, C. et al., "Are there predictors of Remicade treatment success or failure?," Advanced Drug Delivery Reviews, Elsevier B.V., 57(2):237-245, 2005.
Hamilton et al.: Serologic antibodies in relation to outcome in postoperative Crohn's disease. Journal of Gastroenterology and Hepatology. 32:1195-1203 (2017).
Targan et al., Antibodies to CBir1 flagellin define a unique response that is associated independently with complicated Crohn's disease. Gastroenterology 128:2020-20289 (2005).

* cited by examiner

*Primary Examiner* — Lisa V Cook
(74) *Attorney, Agent, or Firm* — Wilson Sonsini Goodrich & Rosati

(57) ABSTRACT

The present invention provides methods for predicting post-operative recurrence of Crohn's disease (CD) in a subject. With the present invention it is possible to predict whether a patient undergoing surgical treatment of CD is at risk of developing histological, radiographic, endoscopic, and/or clinical recurrence of the disease.

16 Claims, 4 Drawing Sheets

Specification includes a Sequence Listing.

METHODS FOR PREDICTING POST-OPERATIVE RECURRENCE OF CROHN'S DISEASE

CROSS-REFERENCE TO RELATED APPLICATIONS

The present application is a continuation of PCT/IB2014/066532, filed Dec. 2, 2014, which application claims priority to U.S. Provisional Patent Application No. 61/911,410, filed Dec. 3, 2013, the contents both of which are hereby incorporated by reference in its entirety for all purposes.

BACKGROUND OF THE INVENTION

A majority of Crohn's disease (CD) patients will require a partial bowel resection during their disease course. Most of these patients will experience a post-operative recurrence of the disease. Multiple methods for detecting recurrence are utilized in the field. For example, endoscopy within the first year after surgery can reveal new epithelial lesions. The severity of these lesions predicts the recurrence of clinical symptoms and the need for additional surgical intervention. Alternatively, recurrence can be detected or predicted using radiographic or histological techniques.

Since the above techniques are a burden to the post-operative patient, predictors of endoscopic, radiographic, or histological recurrence and alternative predictors of clinical recurrence are warranted. A wide range of clinical, serological, and histological features have been identified. However, the literature often provides conflicting data regarding the efficacy of these features or combinations thereof for prediction of recurrence.

BRIEF SUMMARY OF THE INVENTION

The present invention provides a method for predicting post-operative recurrence of Crohn's disease (CD) in a subject. With the present invention it is possible to predict whether a patient undergoing surgical treatment of CD is likely to suffer, for example, histological, radiographic, endoscopic, or clinical recurrence of the disease.

In one aspect, the present invention provides a method for predicting post-operative recurrence of Crohn's Disease (CD) in a subject with CD, the method comprising:
(a) detecting the presence or level of one or more serological markers in a sample from the subject, wherein the one or more serological markers includes one or more anti-flagellin antibodies; and
(b) predicting a risk of post-operative recurrence of CD in the subject based upon the presence or level of the one or more serological markers.

In some aspects of the foregoing embodiment, the one or more serological markers further includes pANCA.

In some embodiments of the foregoing aspect, the sample is a pre-operative sample.

In some cases, the one or more anti-flagellin antibodies is selected from the group consisting of anti-Fla2 antibodies, anti-FlaX antibodies, anti-CBir1 antibodies, and combinations thereof. In some cases, the one or more anti-flagellin antibodies is selected from the group consisting of anti-Fla2 antibodies and anti-FlaX antibodies. In some cases, the one or more serological markers further includes ASCA-IgA, ASCA-IgG, anti-OmpC antibodies, CRP, or combinations thereof.

In some cases, the method further comprises determining the presence or absence of one or more clinical markers. For example, the one or more clinical markers can include active smoking.

In some cases, the subject is predicted to have an increased risk of post-operative recurrence of CD if the level of the one or more anti-flagellin antibodies is elevated relative to a mean level for healthy individuals and/or relative to a mean level for CD patients.

In some cases, the subject is predicted to have an increased risk of post-operative recurrence of CD if one or more additional serological markers is present or has an elevated level relative to a mean level for healthy individuals and/or relative to a mean level for CD patients. In some cases, the one or more additional serological markers includes pANCA, and the sample is pANCA positive.

In some cases, the method further comprises determining the presence or absence of one or more clinical markers. For example, in some cases, the one or more clinical markers includes active smoking and the subject is predicted to have an increased risk of post-operative recurrence of CD if the subject is an active smoker.

In some cases, the subject is predicted to have an increased risk of post-operative recurrence of CD if the level of the one or more anti-flagellin antibodies is at least in the third quartile of the anti-flagellin antibody levels for healthy individuals and/or CD patients.

In some cases, the subject has undergone an intestinal resection.

In one embodiment of any of the foregoing aspects, embodiments, or cases, section (b) comprises predicting a risk of post-operative recurrence of CD in the subject by calculating a risk score based upon the presence or level of the one of more serological markers. For example, in some cases, the risk score is based upon the presence or level of two or more serological markers. In some cases, the risk score is further based upon the presence or absence of one or more clinical markers. In some cases, the one of more serological markers is a combination of an anti-flagellin antibody and pANCA, and the one or more clinical markers is whether the subject is an active smoker. In some cases, a higher risk score is predictive of an increased risk of post-operative recurrence of CD.

In another aspect, the present invention provides a method for predicting post-operative recurrence of Crohn's disease (CD) in a subject with CD, the method comprising:
(a) determining the presence of a first risk factor by detecting an elevated level of an anti-flagellin antibody in a sample from the subject;
(b) determining the presence of a second risk factor by detecting the presence of pANCA in the sample;
(c) determining the presence of a third risk factor by determining whether the subject is an active smoker; and
(d) predicting a risk of post-operative recurrence of CD in the subject based upon the presence of the first, second, and third risk factors,
wherein the presence of one of the risk factors is predictive of an increased risk of post-operative recurrence of CD, wherein the presence of two of the risk factors is predictive of a greater risk of post-operative recurrence of CD relative to the presence of one of the risk factors, and wherein the presence of three of the risk factors is predictive of greater risk of post-operative recurrence of CD relative to the presence of two of the risk factors.

In particular embodiments, the level of the anti-flagellin antibody is elevated if the level is at least in the third quartile of the anti-flagellin antibody level for healthy individuals and/or CD patients. In some cases, the anti-flagellin antibody is selected from the group consisting of an anti-CBir1 antibody, anti-FlaX antibody, anti-Fla2 antibody, and combinations thereof.

In particular embodiments, steps (a), (b), and (c) are performed in any order.

In some cases, the method further comprises detecting the presence or level of ASCA-IgA, ASCA-IgG, anti-OmpC antibodies, and/or CRP in the sample.

In some cases, the subject has undergone an intestinal resection.

In any of the foregoing aspects, embodiments, or cases, the sample can be whole blood, serum, or plasma.

In yet another aspect, the present invention provide a method for predicting post-operative recurrence of Crohn's disease (CD) in a subject with CD, the method comprising:
   (a) detecting the presence or level of one or more serological markers in a sample from the subject, wherein the one or more serological markers includes OmpC; and
   (b) predicting a risk of post-operative recurrence of CD in the subject based upon the presence or level of the one or more serological markers.

In certain instances, the method further includes pANCA as a serological marker.

In any of the foregoing aspects, embodiments, or cases, the post-operative recurrence can comprise endoscopic recurrence (ER), histological recurrence (HR), and/or clinical recurrence (CR).

Other objects, features, and advantages of the present invention will be apparent to one of skill in the art from the following detailed description and figures.

DETAILED DESCRIPTION OF THE INVENTION

I. INTRODUCTION

Figure 1:
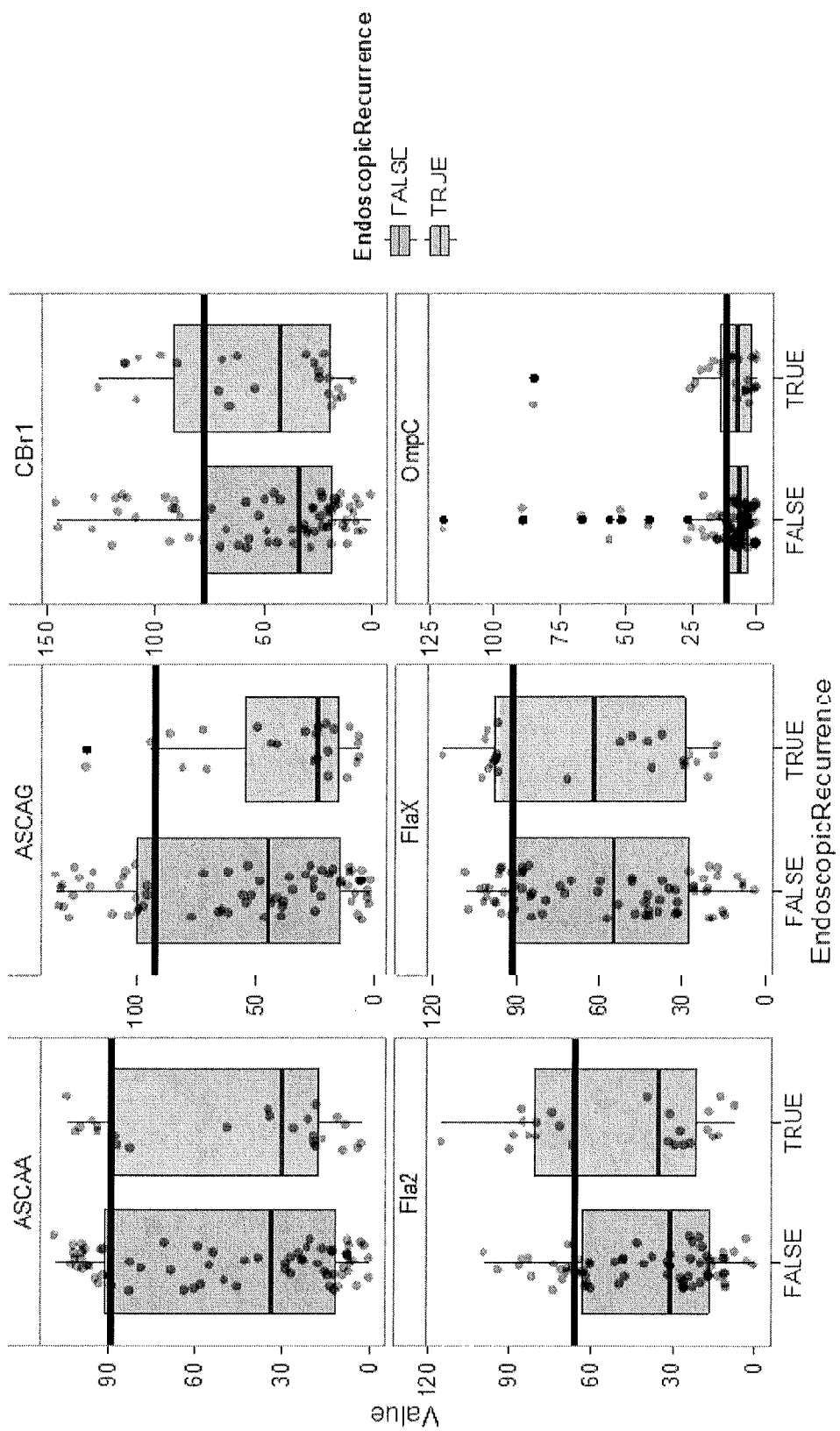
FIG. 1 depicts a boxplot comparing the indicated marker levels and whether the patient experienced endoscopic recurrence at 6 months.

Crohn's disease (CD) is a disease of chronic inflammation that can involve any part of the gastrointestinal tract. Commonly, the distal portion of the small intestine, i.e., the ileum, and the cecum are affected. In other cases, the disease is confined to the small intestine, colon, or anorectal region. CD occasionally involves the duodenum and stomach, and more rarely the esophagus and oral cavity.

The variable clinical manifestations of CD are, in part, a result of the varying anatomic localization of the disease. The most frequent symptoms of CD are abdominal pain, diarrhea, and recurrent fever. CD is commonly associated with intestinal obstruction or fistula, an abnormal passage between diseased loops of bowel. CD also includes complications such as inflammation of the eye, joints, and skin, liver disease, kidney stones, and amyloidosis. In addition, CD is associated with an increased risk of intestinal cancer.

Several features are characteristic of the pathology of CD. The inflammation associated with CD, known as transmural inflammation, involves all layers of the bowel wall. Thickening and edema, for example, typically also appear throughout the bowel wall, with fibrosis present in long-standing forms of the disease. The inflammation characteristic of CD is discontinuous in that segments of inflamed tissue, known as "skip lesions," are separated by apparently normal intestine. Furthermore, linear ulcerations, edema, and inflammation of the intervening tissue lead to a "cobblestone" appearance of the intestinal mucosa, which is distinctive of CD.

A hallmark of CD is the presence of discrete aggregations of inflammatory cells, known as granulomas, which are generally found in the submucosa. Some CD cases display typical discrete granulomas, while others show a diffuse granulomatous reaction or a nonspecific transmural inflammation. As a result, the presence of discrete granulomas is indicative of CD, although the absence of granulomas is also consistent with the disease. Thus, transmural or discontinuous inflammation, rather than the presence of granulomas, is a preferred diagnostic indicator of CD (Rubin and Farber, Pathology (Second Edition), Philadelphia, J.B. Lippincott Company (1994)).

Crohn's disease may be categorized by the behavior of disease as it progresses. This was formalized in the Vienna classification of Crohn's disease. See, Gasche et al., *Inflamm. Bowel Dis.*, 6:8-15 (2000). There are three categories of disease presentation in Crohn's disease: (1) stricturing, (2) penetrating, and (3) inflammatory. Stricturing disease causes narrowing of the bowel which may lead to bowel obstruction or changes in the caliber of the feces. Penetrating disease creates abnormal passageways (fistulae) between the bowel and other structures such as the skin. Inflammatory disease (also known as non-stricturing, non-penetrating disease) causes inflammation without causing strictures or fistulae.

As such, Crohn's disease represents a number of heterogeneous disease subtypes that affect the gastrointestinal tract and may produce similar symptoms. As used herein in reference to CD, the term "clinical subtype" includes a classification of CD defined by a set of clinical criteria that distinguish one classification of CD from another. As non-limiting examples, subjects with CD can be classified as having stricturing (e.g., internal stricturing), penetrating (e.g., internal penetrating), or inflammatory disease as described herein, or these subjects can additionally or alternatively be classified as having fibrostenotic disease, small bowel disease, internal perforating disease, perianal fistulizing disease, UC-like disease, the need for small bowel surgery, the absence of features of UC, or combinations thereof.

In certain instances, subjects with CD can be classified as having complicated CD, which is a clinical subtype characterized by stricturing or penetrating phenotypes. In certain other instances, subjects with CD can be classified as having a form of CD characterized by one or more of the following complications: fibrostenosis, internal perforating disease, and the need for small bowel surgery. In further instances, subjects with CD can be classified as having an aggressive form of fibrostenotic disease requiring small bowel surgery. Criteria relating to these subtypes have been described, for example, in Gasche et al., *Inflamm. Bowel Dis.*, 6:8-15 (2000); Abreu et al., *Gastroenterology*, 123:679-688 (2002); Vasiliauskas et al., *Gut*, 47:487-496 (2000); Vasiliauskas et al., *Gastroenterology*, 110:1810-1819 (1996); and Greenstein et al., *Gut*, 29:588-592 (1988).

The "fibrostenotic subtype" of CD is a classification of CD characterized by one or more accepted characteristics of fibrostenosing disease. Such characteristics of fibrostenosing disease include, but are not limited to, documented persistent intestinal obstruction or an intestinal resection for an intestinal obstruction. The fibrostenotic subtype of CD can be accompanied by other symptoms such as perforations, abscesses, or fistulae, and can further be characterized by persistent symptoms of intestinal blockage such as nausea, vomiting, abdominal distention, and inability to eat solid food. Intestinal X-rays of patients with the fibrostenotic subtype of CD can show, for example, distention of the bowel before the point of blockage.

The requirement for small bowel surgery in a subject with the fibrostenotic subtype of CD can indicate a more aggressive form of this subtype. Additional subtypes of CD are also known in the art and can be identified using defined clinical criteria. For example, internal perforating disease is a clinical subtype of CD defined by current or previous evidence of entero-enteric or entero-vesicular fistulae, intra-abdominal abscesses, or small bowel perforation. Perianal perforating disease is a clinical subtype of CD defined by current or previous evidence of either perianal fistulae or abscesses or rectovaginal fistula. The UC-like clinical subtype of CD can be defined by current or previous evidence of left-sided colonic involvement, symptoms of bleeding or urgency, and crypt abscesses on colonic biopsies. Disease location can be classified based on one or more endoscopic, radiologic, or histological studies.

One skilled in the art understands that overlap can exist between clinical subtypes of CD and that a subject having CD can have more than one clinical subtype of CD. For example, a subject having CD can have the fibrostenotic subtype of CD and can also meet clinical criteria for a clinical subtype characterized by the need for small bowel surgery or the internal perforating disease subtype. Similarly, the markers described herein can be associated with more than one clinical subtype of CD.

In certain instances, surgery may be required to treat complications of CD such as obstructions, fistulas, or abscesses. In other instances, surgery may be required if the disease does not respond to drug treatment. Although patients may undergo remission after surgery, CD is not generally cured by surgery, and recurrence can occur. Patients that are likely to experience recurrence may benefit from prophylactic drug treatment or changes in lifestyle.

Preventing or predicting post-operative endoscopic (ER), histological (HR), or clinical recurrence (CR) remains a challenging issue in patients with Crohn's disease (CD) undergoing surgical intervention (e.g., intestinal resection). Several clinical and histological risk factors have been identified, and may guide selection of appropriate candidates for post-operative prophylactic CD therapy. For example, serological markers have been associated with more complicated and aggressive CD behavior. Consequently, a set of pre-operative serological markers have been evaluated to determine whether they, or a subset thereof, could strengthen the prediction of post-operative ER, HR, or CR. Additionally, the serological markers have been combined with clinical markers to strengthen the prediction of post-operative ER, HR, or CR.

II. DEFINITIONS

As used herein, the following terms have the meanings ascribed to them unless specified otherwise.

The term "individual," "subject," or "patient" typically refers to humans, but also to other animals including, e.g., other primates, rodents, canines, felines, equines, ovines, porcines, and the like.

The term "sample" includes any biological specimen obtained from an individual. Suitable samples for use in the present invention include, without limitation, whole blood, plasma, serum, saliva, urine, stool, tears, any other bodily fluid, tissue samples (e.g., biopsy), and cellular extracts thereof (e.g., red blood cellular extract). In a preferred embodiment, the sample is a serum sample. The use of samples such as serum, saliva, and urine is well known in the art (see, e.g., Hashida et al., *J. Clin. Lab. Anal.*, 11:267-86 (1997)). One skilled in the art will appreciate that samples such as serum samples can be diluted or concentrated prior to the analysis of marker levels. In some cases, samples are pre-operative samples. In such cases, the patient may have subsequently undergone surgery to correct or mitigate CD, such as an intestinal resection, a hemicolectomy, or a right hemicolectomy. In other cases, the samples are post-operative samples. In such cases, the patient may have previously undergone surgery to correct or mitigate CD, such as an intestinal resection, a hemicolectomy, or a right hemicolectomy.

The term "predicting" includes determining a likelihood that an event will occur. For example, a patient can be predicted to have an increased risk of endoscopic, histological, or clinical recurrence of CD. In certain instances, "predicting" is based on statistical evidence, empirical evidence (e.g., presence, absence, or level of one or more markers), or both. In certain embodiments, a subject can be predicted as having a risk of post-operative CD recurrence, an increased risk of post-operative CD recurrence, or a decreased risk of post-operative CD recurrence. In some cases, the increased or decreased risk is relative to the mean or median likelihood of an event happening to a similarly situated subject. For example, a subject can be predicted to have an increased or decreased risk of post-operative recurrence of CD relative to the mean or median likelihood of post-operative recurrence of CD.

In some embodiments, predicting includes calculating a risk score based upon the presence, absence, or level of one or more markers (e.g., one or more serological and/or clinical markers). For example, the risk score can be based on the presence, absence or level of one or more anti-flagellin antibodies (e.g., anti-CBir-1, anti-FlaX, or anti-Fla2). As another example, the risk score can be based on the presence, absence or level of one or more anti-neutrophil antibodies (e.g., ANCA, pANCA, cANCA, NSNA, SAPPA, etc.). As another example, the risk score can be based on the presence absence or level of one or more anti-*Saccharomyces cerevisiae* antibodies (e.g., ASCA-IgA, ASCA-IgG, ASCA-IgM, etc.). As yet another example, the risk score can be based on the presence absence or level of one or more anti-microbial antibodies (e.g., anti-OmpA antibodies, anti-OmpC antibodies, anti-flagellin antibodies, anti-I2 antibodies, etc.). As yet another example, the risk score can be based on the presence, absence, or level of C-reactive protein (CRP). In some cases, the risk score can be based on any combination of the above markers. As another example, the risk score can be based on the presence, absence, or level of one or more clinical markers, such as whether the patient is an active smoker. In some cases, the risk score is a cumulative risk score based upon the presence, absence, or level of two, three, or more serological and/or clinical markers. In a preferred embodiment, the risk score is based on the presence of pANCA, the level of an anti-flagellin antibody (e.g., anti-CBir-1, anti-FlaX, or anti-Fla2), and whether the patient is an active smoker.

The term "recurrence" in the context of CD includes post-operative recurrence. For example, recurrence can refer to recurrence of CD after surgical intervention. Non limiting examples of surgical intervention include intestinal resection, or colectomy (e.g., right hemicolectomy). Recurrence includes histological recurrence, endoscopic recurrence, radiographic recurrence, or clinical recurrence.

In some embodiments, a patient is considered to exhibit endoscopic recurrence if the patient exhibits a Rutgeert's score of at least about i2, i3 (e.g., diffuse apthous ileitis), or i4 (e.g., diffuse inflammation with larger ulcers, nodules, and/or narrowing). The Rutgeert's score is described in, e.g., Rutgeerts et al., *Gastroenterology*, 99(4):956-63 (1990); and Marshal, *Can. J. Gastroenterol.*, 20(6): 399-400 (2006).

Histological recurrence includes recurrence of Crohn's disease that is detectable by histological examination of intestinal or colon tissue biopsies. In some cases, histological recurrence occurs when one or more tissue biopsies exhibit granulomatous enteritis characteristic of CD. Radiographic recurrence includes the occurrence of new lesions as assessed by radiographic imaging techniques.

In some embodiments, a patient is considered to exhibit clinical recurrence if the patient exhibits a Crohn's Disease Activity Index (CDAI) of at least about 151. In some embodiments, a patient is considered to exhibit a clinical recurrence if the patient exhibits a CDAI increase of at least about 70 points. In some embodiments, a patient is considered to exhibit a clinical recurrence if the patient exhibits a Harvey Bradshaw index of at least about 4, 5, 6, or 7. In some embodiments, clinical recurrence is detected or measured using the Simple Index of Crohn's Disease activity. See, e.g., Elliott et al., *Lancet*, 1(8173):876 (1980).

The term "marker" includes any biochemical marker, serological marker, genetic marker, or other clinical or echographic characteristic that can be used to classify a sample as predictive of (e.g., predictive of an increased risk of) endoscopic, histological, and/or clinical recurrence of Crohn's disease. Non-limiting examples of serological markers suitable for use in the present invention are described below and include anti-flagellin antibodies (e.g., anti-CBir-1, anti-FlaX, or anti-Fla2), anti-neutrophil antibodies (e.g., ANCA, pANCA, cANCA, NSNA, SAPPA, etc.), anti-*Saccharomyces cerevisiae* antibodies (e.g., ASCA-IgA, ASCA-IgG, ASCA-IgM, etc.), antimicrobial antibodies (e.g., anti-OmpA antibodies, anti-OmpC antibodies, anti-flagellin antibodies, anti-I2 antibodies, etc.), acute phase proteins (e.g., CRP), apolipoproteins (e.g., SAA), defensins (e.g., β defensin), growth factors (e.g., EGF, VEGF), cytokines (e.g., TWEAK, IL-113, IL-6), cadherins (e.g., E-cadherin), cellular adhesion molecules (e.g., ICAM-1, VCAM-1); genetic markers (e.g., SNPs) such as ATG16L1, ECM1, NKX2-3, STAT3, and NOD2/CARD15; and combinations thereof. Non-limiting examples of genetic markers also include variant alleles in the GLI1 (e.g., rs2228224 and/or rs2228226), MDR1 (e.g., rs2032582), ATG16L1 (e.g., rs2241880, rs3828309), ECM1 (e.g., rs7511649, rs373240, rs13294), NKX2-3 (e.g., rs1190140, rs10883365, rs6584283), STAT3 (e.g., rs744166), and NOD2/CARD15 (e.g., rs2066847, rs2066845, rs5743293) genes.

Non-limiting examples of clinical markers are described below and include whether a patient is an active smoker. Additional examples of clinical markers include, without limitation, diarrhea, abdominal pain, cramping, fever, anemia, weight loss, anxiety, depression, and combinations thereof. In some embodiments, a prediction of ER, HR, or CR is based upon a combination of analyzing a sample obtained from an individual to determine the presence, absence, level, or genotype of one or more markers and determining whether the individual has one or more clinical factors. One skilled in the art will know of additional clinical or serological markers suitable for use in the present invention.

In some embodiments, the markers are utilized in combination with one or more (e.g., a plurality of) statistical analyses to aid or provide a prediction of CD recurrence in an individual. In certain instances, the individual can be predicted to exhibit clinical recurrence (CR), predicted to exhibit histological recurrence (HR), or predicted to exhibit endoscopic recurrence (ER). For example, the prediction can provide a probability of ER, HR, or CR. In certain other instances, the prediction can be the likelihood of long-term recovery from the disease (e.g., the likelihood of remission). In some embodiments, markers (e.g., serological or clinical markers) are referred to as "risk factors."

As used herein, the term "anti-flagellin antibody" includes antibodies directed to a protein component of bacterial flagella as described in, e.g., PCT Patent Publication No. WO 03/053220 and U.S. Pat. No. 7,361,733 incorporated herein by reference. The term "flagellin" includes a bacterial flagellum protein that is immunoreactive with an anti-flagellin antibody. Microbial flagellins are proteins found in bacterial flagellum that arrange themselves in a hollow cylinder to form a filament.

The term "transforming the sample" includes a physical or chemical change of the sample to extract a marker as defined herein. An extraction, a manipulation, a chemical precipitation, an ELISA, an immuno-extraction, a physical or chemical modification of the sample to measure a marker all constitute a transformation. As long as the sample is not identical before and after the transformation step, the change is a transformation.

As used herein, the term "substantially the same amino acid sequence" includes an amino acid sequence that is similar, but not identical to, the naturally-occurring amino acid sequence. For example, an amino acid sequence, i.e., polypeptide, that has substantially the same amino acid sequence as a Fla2 protein or fragment thereof can have one or more modifications such as amino acid additions, deletions, or substitutions relative to the amino acid sequence of the naturally-occurring, provided that the modified polypeptide retains substantially at least one biological activity of a Fla2 protein such as immunoreactivity. Comparison for substantial similarity between amino acid sequences is usually performed with sequences between about 6 and 100 residues, preferably between about 10 and 100 residues, and more preferably between about 25 and 35 residues. A particularly useful modification of a polypeptide of the present invention, or a fragment thereof, is a modification that confers, for example, increased stability. Incorporation of one or more D-amino acids is a modification useful in increasing stability of a polypeptide or polypeptide fragment. Similarly, deletion or substitution of lysine residues can increase stability by protecting the polypeptide or polypeptide fragment against degradation.

As used herein, the term "antibody" includes a population of immunoglobulin molecules, which can be polyclonal or monoclonal and of any isotype (e.g., IgA, IgD, IgE, IgG, or IgM), or an immunologically active fragment of an immunoglobulin molecule. Such an immunologically active fragment contains the heavy and light chain variable regions, which make up the portion of the antibody molecule that specifically binds an antigen. For example, an immunologically active fragment of an immunoglobulin molecule known in the art as Fab, Fab' or F(ab')$_2$ is included within the meaning of the term antibody.

As used herein, "quartile sum score" or "QSS" includes the sum of quartile scores for all of the markers of interest. As a non-limiting example, a quartile sum score for a panel of 3 markers (e.g., serological, protein, and/or clinical) may range from 3-12, wherein each of the individual markers is assigned a quartile score (Q) of 1-4 based upon the presence or absence of the marker, the concentration level of the marker, or the genotype of the marker.

In some embodiments, each serological marker's Q3 (third quartile) value from a dataset of pre-operative samples from CD patients is used as a cutoff. In such embodiments, samples exhibiting a level of a serological marker below the cutoff are considered negative for the marker. Similarly, samples exhibiting a level of the marker above the cutoff are considered positive for the marker. The presence (i.e., sample is above the Q3 cutoff value) or absence (i.e., sample is below the Q3 cutoff value) of the marker can then be used, e.g., in combination with one or more other markers, to predict ER, HR, or CR.

III. METHODS

The present invention is based, in part, on the surprising discovery that the likelihood of a subject experiencing a post-operative recurrence of Crohn's disease (CD) can be accurately predicted by detecting the presence, absence, or level, of one or more diagnostic serological or clinical markers. In some cases, the accuracy can be further improved as additional serological or clinical markers are utilized. For example, in some embodiments, the likelihood of a subject experiencing a post-operative recurrence of CD can be accurately predicted by detecting the presence, absence, or level of one or more anti-flagellin antibodies (e.g., anti-CBir-1, anti-FlaX, or anti-Fla2). In some embodiments, the likelihood of a subject experiencing a post-operative recurrence of CD can be accurately predicted by detecting the presence, absence, or level of one or more anti-neutrophil antibodies (e.g., ANCA, pANCA, cANCA, NSNA, SAPPA, etc.). In some cases, the prediction can be improved by determining the presence, absence, or level of an anti-flagellin antibody and an anti-neutrophil antibody. In some cases, the prediction can include utilizing one or more clinical markers, such as whether the patient is an active smoker.

In some embodiments, anti-flagellin antibody levels (e.g., anti-Flat, anti-FlaX, or anti-CBir1) in a sample are determined. The level of anti-flagellin antibody present in a sample can be measured using a flagellin protein or a fragment thereof such as an immunoreactive fragment thereof. Suitable flagellin antigens useful in measuring anti-flagellin antibody levels in a sample include, without limitation, a flagellin protein such as CBir-1 flagellin, flagellin X, flagellin A, flagellin Fla2, flagellin B, fragments thereof, and combinations thereof, a flagellin polypeptide having substantially the same amino acid sequence as one of the foregoing flagellin proteins, or a fragment thereof such as an immunoreactive fragment thereof.

In one embodiment, the present invention provides a method for predicting post-operative recurrence of Crohn's disease (CD) in a subject with CD, the method comprising:
(a) detecting the presence or level of one or more serological markers in a sample from the subject, wherein the one or more serological markers includes one or more anti-flagellin antibodies; and
(b) predicting a risk of post-operative recurrence of CD in the subject based upon the presence or level of the one or more serological markers.

In a preferred aspect, the sample is a pre-operative sample.

In another embodiment, the present invention provides a method for predicting post-operative recurrence of Crohn's disease (CD) in a subject with CD, the method comprising:
(a) determining the presence of a first risk factor by detecting an elevated level of an anti-flagellin antibody in a sample from the subject;
(b) determining the presence of a second risk factor by detecting the presence of pANCA in the sample;
(c) determining the presence of a third risk factor by determining whether the subject is an active smoker; and
(d) predicting a risk of post-operative recurrence of CD in the subject based upon the presence of the first, second, and third risk factors,
wherein the presence of one of the risk factors is predictive of an increased risk of post-operative recurrence of CD, wherein the presence of two of the risk factors is predictive of a greater risk of post-operative recurrence of CD relative to the presence of one of the risk factors, and wherein the presence of three of the risk factors is predictive of greater risk of post-operative recurrence of CD relative to the presence of two of the risk factors.

In some embodiments, the method of the present invention entails analysis of a sample selected from the group consisting of whole blood, tissue, saliva, cheek cells, hair, fluid, plasma, serum, cerebrospinal fluid, buccal swabs, mucus, urine, stools, spermatozoids, vaginal secretions, lymph, amniotic fluid, pleural liquid, tears, and combinations thereof.

In some embodiments, the method of the present invention entails analysis of a sample collected and analyzed before surgery (pre-operative). For example, in certain instances, the sample is collected about 1 month to about 3 years before surgery, or about 3 months to 12 months before surgery. In other aspects, the collection and analysis is performed about 1, 2, 3, 4, 5, 6, 7, 8, 9, 10, 11 or 12 months before surgery. In certain instances, the sample can be collected and analyzed 1-3 weeks before, or two weeks before, or 1 week before surgery, or even a few days before such as 1, 2, 3, 4, 5, or 6 days before surgery.

In some embodiments, the method of the present invention entails collection and analysis about 1 month to about 3 years after surgery, or about 3 months to 12 months after surgery (post-operative). In other aspects, the collection and analysis is performed about 1, 2, 3, 4, 5, 6, 7, 8, 9, 10, 11 or 12 months or more after surgery.

In yet another aspect, the present invention provide a method for predicting post-operative recurrence of Crohn's disease (CD) in a subject with CD, the method comprising:
(a) detecting the presence or level of one or more serological markers in a sample from the subject, wherein the one or more serological markers includes OmpC; and (b) predicting a risk of post-operative recurrence of CD in the subject based upon the presence or level of the one or more serological markers.

In certain instances, the method further includes pANCA as a serological marker. In other instances, one or more serological markers further includes ASCA-IgA, ASCA-IgG, pANCA, CRP, or combinations thereof.

In certain instances, the post-operative recurrence is clinical recurrence (CR) or endoscopic recurrence (ER).

In certain instances, the sample is a post-operative sample. For example, the sample is collected about 3 months to about 12 months after surgery and analyzed.

In certain instances, the method further comprises determining the presence or absence of one or more clinical markers such as active smoking.

Serological Markers

Anti-Flagellin Antibodies

Any anti-flagellin antibody present in a sample from an individual may be detected in accordance with the methods of the present invention. In some embodiments, the level of anti-Fla2 antibodies is determined. In some cases, the one or more anti-flagellin antibodies includes one or more of anti-Fla2 antibodies, anti-FlaX antibodies, anti-CBir1 antibodies, or combinations thereof. In some cases, the one or more anti-flagellin antibodies includes anti-Fla2, or anti-FlaX, or a combination thereof. In other embodiments, the level of anti-FlaX is determined. In other embodiments, the level of anti-flagellin A, and/or anti-flagellin B antibodies is determined.

The level of anti-flagellin antibody present in a sample from can be determined using a flagellin protein or a fragment thereof such as an immunoreactive fragment thereof. For example, anti-flagellin antibody levels in a sample from an individual can be determined using a flagellin protein or fragment thereof in an immunoassay such as an enzyme-linked immunosorbent assay (ELISA). Suitable flagellin antigens useful in determining anti-flagellin antibody levels in a sample include those described herein. In certain embodiments, the flagellin antigen is a Fla2 flagellin comprising a polypeptide fragment consisting of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, or more contiguous amino acids (including all intermediate lengths) of the full-length Fla2 flagellin sequence set forth in SEQ ID NO:1. Typically, the Flat flagellin polypeptide fragment is immunologically reactive with an antibody that binds to the full-length Fla2 flagellin sequence and/or a T-cell that reacts with the full-length Fla2 flagellin sequence. In some embodiments, the polypeptide fragment is the amino terminal conserved region of the full-length Fla2 flagellin sequence. In other embodiments, the polypeptide fragment is the amino terminal conserved region plus the variable region of the full-length Flat flagellin sequence. In some instances, the Fla2 flagellin antigen is a fusion protein consisting of a Flat flagellin polypeptide fragment described herein and a tag such as a six histidine or glutathione S-transferase (GST) tag. In certain other embodiments, the Fla2 flagellin antigen comprises the amino acid sequence of SEQ ID NO:1 or a sequence having substantial identity thereto (e.g., at least 80%, 85%, 90%, or 95% identity to SEQ ID NO:1).

Anti-CBir-1 antibody levels in a sample from an individual can be determined, for example, using an immunoassay such as an enzyme-linked immunosorbent assay (ELISA). In certain embodiments, the flagellin antigen is a CBir-1 flagellin comprising a polypeptide fragment consisting of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, or more contiguous amino acids (including all intermediate lengths) of the full-length Cbir-1 flagellin sequence set forth in SEQ ID NO:2. Typically, the CBir-1 flagellin polypeptide fragment is immunologically reactive with an antibody that binds to the full-length CBir-1 flagellin sequence and/or a T-cell that reacts with the full-length CBir-1 flagellin sequence. In some embodiments, the polypeptide fragment is the amino terminal conserved region (amino acid residues 1-147) of the sequence set forth in SEQ ID NO:2. In other embodiments, the polypeptide fragment is the amino terminal conserved region plus the variable region (amino acid residues 1-418) of the sequence set forth in SEQ ID NO:2. In some instances, the CBir-1 flagellin antigen is a fusion protein consisting of a CBir-1 flagellin polypeptide fragment described herein and a tag such as a six histidine or glutathione S-transferase (GST) tag.

Anti-FlaX antibody levels in a sample from an individual can be determined, for example, using an immunoassay such as an enzyme-linked immunosorbent assay (ELISA). In certain embodiments, the flagellin antigen is a FlaX flagellin comprising a polypeptide fragment consisting of at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150 or more contiguous amino acids (including all intermediate lengths) of the full-length FlaX flagellin sequence set forth in SEQ ID NO:3. Typically, the FlaX flagellin polypeptide fragment is immunologically reactive with an antibody that binds to the full-length FlaX flagellin sequence and/or a T-cell that reacts with the full-length FlaX flagellin sequence. In some embodiments, the polypeptide fragment is the amino terminal conserved region of the full-length FlaX flagellin sequence. In other embodiments, the polypeptide fragment is the amino terminal conserved region plus the variable region of the full-length FlaX flagellin sequence. In some instances, the FlaX flagellin antigen is a fusion protein consisting of a FlaX flagellin polypeptide fragment described herein and a tag such as a six histidine or glutathione S-transferase (GST) tag.

An "elevated" level of anti-flagellin antibodies is intended to include a detectable increase in the level of a given anti-flagellin antibody (e.g., anti-Fla2, anti-FlaX, or anti-CBir1 antibody) relative to a control. A detectable increase can be about 5%, 10%, 15%, 20%, 25%, 30%, 35%, 40%, 45%, 50%, 55%, 60%, 65%, 70%, 75%, 80%, 85%, 90%, 95%, 100%, or more higher than the level of a given anti-flagellin antibody detected in a control. In some cases, the control is a sample from a healthy subject or a sample known to provide a value similar to a sample from a healthy subject (e.g., a reference sample containing a low, known, amount of anti-flagellin antibody).

An increase in the level of a given anti-flagellin antibody is typically measured using any method or technique known in the art such as an immunoassay or immunohistochemical assay. In preferred embodiments, the immunoassay is an enzyme-linked immunosorbent assay (ELISA). In certain instances, elevated anti-flagellin antibody levels (e.g., elevated anti-FlaX, anti-CBir1, and/or anti-Fla2 antibody levels) include a level above a reference value of about 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, 35.0, 36.0, 37.0, 38.0, 39.0, 40.0, 41.0, 42.0, 43.0, 44.0, 45.0, 46.0, 47.0, 48.0, 49.0, 50.0, 51.0, 52.0, 53.0, 54.0, 55.0, 56.0, 57.0, 58.0, 59.0, 60.0, 61.0, 62.0, 63.0, 64.0, 65.0, 66.0, 67.0, 68.0, 69.0, 70.0, 71.0, 72.0, 73.0, 74.0, 75.0, 76.0, 77.0, 78.0, 79.0, 80.0, 81.0, 82.0, 83.0, 84.0, 85.0, 86.0, 87.0, 88.0, 89.0, 90.0, 91.0, 92.0, 93.0, 94.0, 95.0, 96.0, 97.0, 98.0, 99.0 or 100.0 EU/ml (or any range or fraction therein) when an ELISA is used.

In some preferred embodiments, an elevated level of anti-flagellin antibodies such as an elevated level of anti-Fla2 antibodies is a level above a reference value of about 65.0 EU/ml. In some preferred embodiments, an elevated level of anti-flagellin antibodies such as an elevated level of anti-FlaX antibodies is a level above a reference value of about 91.0 EU/ml. In some preferred embodiments, an elevated level of anti-flagellin antibodies such as an elevated level of anti-CBir1 antibodies is a level above a reference value of about 77 EU/ml.

In some embodiments, the presence of an elevated level of anti-flagellin antibodies (e.g., elevated anti-FlaX, anti-CBir1, and/or anti-Fla2 antibody levels) is associated with an about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40-fold (or any range or fraction therein) increased risk of post-operative recurrence of CD.

In certain embodiments, the anti-flagellin biomarker is a binary rather than a numerical variable since its value is either positive or negative. For example, the value may be positive if it is above a cutoff value (e.g., above a Q3 cutoff value) and negative if it is below a cutoff value (e.g., below a Q3 cutoff value). In some embodiments, an anti-flagellin-positive status is associated with a higher risk of endoscopic, histological, or clinical recurrence.

Anti-Neutrophil Antibodies

In some aspects, the one or more serological markers further includes ANCA (e.g., pANCA). In some cases, the determination of the presence or absence of pANCA in a sample is useful in the present invention. As used herein, the term "anti-neutrophil cytoplasmic antibody" or "ANCA" includes antibodies directed to cytoplasmic and/or nuclear components of neutrophils. ANCA activity can be divided into several broad categories based upon the ANCA staining pattern in neutrophils: (1) cytoplasmic neutrophil staining without perinuclear highlighting (cANCA); (2) perinuclear staining around the outside edge of the nucleus (pANCA); (3) perinuclear staining around the inside edge of the nucleus (NSNA); and (4) diffuse staining with speckling across the entire neutrophil (SAPPA). In certain instances, pANCA staining is sensitive to DNase treatment. The term ANCA encompasses all varieties of anti-neutrophil reactivity, including, but not limited to, cANCA, pANCA, NSNA, and SAPPA. Similarly, the term ANCA encompasses all immunoglobulin isotypes including, without limitation, immunoglobulin A and G. In certain instances, the presence of ANCA predicts patients at higher risk for recurrence. In other instances, the presence of ANCA predicts patients at lower risk for recurrence.

ANCA levels in a sample from an individual can be determined, for example, using an immunoassay such as an enzyme-linked immunosorbent assay (ELISA) with alcohol-fixed neutrophils. The presence or absence of a particular category of ANCA such as pANCA can be determined, for example, using an immunohistochemical assay such as an indirect fluorescent antibody (IFA) assay. Preferably, the presence or absence of pANCA in a sample is determined using an immunofluorescence assay with DNase-treated, fixed neutrophils. In addition to fixed neutrophils, antigens specific for ANCA that are suitable for determining ANCA levels include, without limitation, unpurified or partially purified neutrophil extracts; purified proteins, protein fragments, or synthetic peptides such as histone H1 or ANCA-reactive fragments thereof (see, e.g., U.S. Pat. No. 6,074,835); histone H1-like antigens, porin antigens, *Bacteroides* antigens, or ANCA-reactive fragments thereof (see, e.g., U.S. Pat. No. 6,033,864); secretory vesicle antigens or ANCA-reactive fragments thereof (see, e.g., U.S. patent application Ser. No. 08/804,106); and anti-ANCA idiotypic antibodies. One skilled in the art will appreciate that the use of additional antigens specific for ANCA is within the scope of the present invention.

In certain embodiments, the ANCA biomarker (e.g., pANCA) is a binary rather than a numerical variable since its value is either positive or negative. For example, the value may be positive if it is above a cutoff value (e.g., above a Q3 cutoff value) and negative if it is below a cutoff value (e.g., below a Q3 cutoff value). In some cases, the value is positive if it is detected as present at any level, or detected as present above a background level. In some cases, the value is negative if it is not detected, or not detected above a background level. In some embodiments, a pANCA-positive status is associated with a higher risk of endoscopic, histological, or clinical recurrence.

Anti-*Saccharomyces cerevisiae* Antibodies

The determination of the presence or level of ASCA (e.g., ASCA-IgA, ASCA-IgG, ASCA-IgM, etc.) in a sample can also be useful in the present invention. The term "anti-*Saccharomyces cerevisiae* immunoglobulin A" or "ASCA-IgA" includes antibodies of the immunoglobulin A isotype that react specifically with *S. cerevisiae*. Similarly, the term "anti-*Saccharomyces cerevisiae* immunoglobulin G" or "ASCA-IgG" includes antibodies of the immunoglobulin G isotype that react specifically with *S. cerevisiae*.

The determination of whether a sample is positive for ASCA-IgA or ASCA-IgG is made using an antibody specific for human antibody sequences or an antigen specific for ASCA. Such an antigen can be any antigen or mixture of antigens that is bound specifically by ASCA-IgA and/or ASCA-IgG. Although ASCA antibodies were initially characterized by their ability to bind *S. cerevisiae*, those of skill in the art will understand that an antigen that is bound specifically by ASCA can be obtained from *S. cerevisiae* or from a variety of other sources so long as the antigen is capable of binding specifically to ASCA antibodies. Accordingly, exemplary sources of an antigen specific for ASCA, which can be used to determine the levels of ASCA-IgA and/or ASCA-IgG in a sample, include, without limitation, whole killed yeast cells such as *Saccharomyces* or *Candida* cells; yeast cell wall mannan such as phosphopeptidomannan (PPM); oligosachharides such as oligomannosides; neoglycolipids; anti-ASCA idiotypic antibodies; and the like. Different species and strains of yeast, such as *S. cerevisiae* strain Su1, Su2, CBS 1315, or BM 156, or *Candida albicans* strain VW32, are suitable for use as an antigen specific for ASCA-IgA and/or ASCA-IgG. Purified and synthetic antigens specific for ASCA are also suitable for use in determining the levels of ASCA-IgA and/or ASCA-IgG in a sample. Examples of purified antigens include, without limitation, purified oligosaccharide antigens such as oligomannosides. Examples of synthetic antigens include, without limitation, synthetic oligomannosides such as those described in U.S. Patent Publication No. 20030105060, e.g., D-Man β(1-2) D-Man β(1-2) D-Man β(1-2) D-Man-OR, D-Man α(1-2) D-Man α(1-2) D-Man α(1-2) D-Man-OR, and D-Man α(1-3) D-Man α(1-2) D-Man α(1-2) D-Man-OR, wherein R is a hydrogen atom, a $C_1$ to $C_{20}$ alkyl, or an optionally labeled connector group.

Preparations of yeast cell wall mannans, e.g., PPM, can be used in determining the levels of ASCA-IgA and/or ASCA-IgG in a sample. Such water-soluble surface antigens can be prepared by any appropriate extraction technique known in the art, including, for example, by autoclaving, or can be obtained commercially (see, e.g., Lindberg et al., *Gut*, 33:909-913 (1992)). The acid-stable fraction of PPM is also useful in the statistical algorithms of the present invention (Sendid et al., *Clin. Diag. Lab. Immunol.*, 3:219-226 (1996)). An exemplary PPM that is useful in determining ASCA levels in a sample is derived from *S. uvarum* strain ATCC #38926.

Purified oligosaccharide antigens such as oligomannosides can also be useful in determining the levels of ASCA-IgA and/or ASCA-IgG in a sample. The purified oligomannoside antigens are preferably converted into neoglycolipids as described in, for example, Faille et al., *Eur. Microbiol. Infect. Dis.*, 11:438-446 (1992). One skilled in the art understands that the reactivity of such an oligomannoside antigen with ASCA can be optimized by varying the mannosyl chain length (Frosh et al., *Proc Natl. Acad. Sci. USA*, 82:1194-1198 (1985)); the anomeric configuration (Fukazawa et al., In "Immunology of Fungal Disease," E. Kurstak (ed.), Marcel Dekker Inc., New York, pp. 37-62 (1989); Nishikawa et al., *Microbiol. Immunol.*, 34:825-840 (1990); Poulain et al., *Eur. J. Clin. Microbiol.*, 23:46-52 (1993); Shibata et al., *Arch. Biochem. Biophys.*, 243:338-348 (1985); Trinel et al., *Infect. Immun.*, 60:3845-3851 (1992)); or the position of the linkage (Kikuchi et al., *Planta*, 190:525-535 (1993)).

Suitable oligomannosides for use in the methods of the present invention include, without limitation, an oligomannoside having the mannotetraose Man(1-3) Man(1-2) Man (1-2) Man. Such an oligomannoside can be purified from PPM as described in, e.g., Faille et al., supra. An exemplary neoglycolipid specific for ASCA can be constructed by releasing the oligomannoside from its respective PPM and subsequently coupling the released oligomannoside to 4-hexadecylaniline or the like.

In certain embodiments, the ASCA biomarker (e.g., ASCA-A, ASCA-G) is a binary rather than a numerical variable since its value is either positive or negative. For example, the value may be positive if it is above a cutoff value (e.g., above a Q3 cutoff value) and negative if it is below a cutoff value (e.g., below a Q3 cutoff value). In some embodiments, an ASCA-positive status is associated with a higher risk of endoscopic, histological, or clinical recurrence.

Anti-Microbial Antibodies

The determination of the presence or level of an anti-OmpC antibody in a sample can be useful in the present invention. As used herein, the term "anti-outer membrane protein C antibody" or "anti-OmpC antibody" includes antibodies directed to a bacterial outer membrane porin as described in, e.g., U.S. Pat. No. 7,138,237 and PCT Patent Publication No. WO 01/89361. The term "outer membrane protein C" or "OmpC" refers to a bacterial porin that is immunoreactive with an anti-OmpC antibody. The term anti-OmpC antibody encompasses all immunoglobulin isotypes including, without limitation, immunoglobulin A and G. Preferably, the presence or level of anti-OmpC IgA is determined.

The level of anti-OmpC antibody present in a sample from an individual can be determined using an OmpC protein or a fragment thereof such as an immunoreactive fragment thereof. Suitable OmpC antigens useful in determining anti-OmpC antibody levels in a sample include, without limitation, an OmpC protein, an OmpC polypeptide having substantially the same amino acid sequence as the OmpC protein, or a fragment thereof such as an immuno-reactive fragment thereof. As used herein, an OmpC polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with an OmpC protein, with the amino acid identity determined using a sequence alignment program such as CLUSTALW. Such antigens can be prepared, for example, by purification from enteric bacteria such as *E. coli*, by recombinant expression of a nucleic acid such as Genbank Accession No. K00541, by synthetic means such as solution or solid phase peptide synthesis, or by using phage display. Determination of anti-OmpC antibody levels in a sample can be done by using an ELISA assay or a histological assay.

The determination of anti-OmpA antibody levels in a sample can be useful in the methods of invention. As used herein, the term "OmpA antigen" or "OmpA" includes a protein that has at least about 50% amino acid identity with *E. coli* OmpA. As a non-limiting example, an OmpA antigen can have at least about 60%, 65%, 70%, 75%, 80%, 85%, 90%, 91%, 92%, 93%, 94%, 95%, 96%, 97%, 98% or 99% amino acid identity with *E. coli* OmpA. For use in the methods of the present invention, an OmpA antigen can be partially purified, for example, by spheroplast lysis from OmpA, or can be similarly prepared from a variety of other *E. coli* strains, which can contain OmpA. An OmpA antigen also can be prepared recombinantly by expressing an encoding nucleic acid sequence such as that available as GenBank accession V00307.1 using methods well known in the art (see, for example, Ausubel et al., Current Protocols in Molecular Biology John Wiley & Sons, Inc. New York (1999)).

The determination of the presence or level of anti-I2 antibody in a sample can also be useful in the present invention. As used herein, the term "anti-I2 antibody" includes antibodies directed to a microbial antigen sharing homology to bacterial transcriptional regulators as described in, e.g., U.S. Pat. No. 6,309,643. The term "I2" refers to a microbial antigen that is immunoreactive with an anti-I2 antibody. The microbial I2 protein is a polypeptide of 100 amino acids sharing some similarity weak homology with the predicted protein 4 from *C. pasteurianum*, Rv3557c from *Mycobacterium tuberculosis*, and a transcriptional regulator from *Aquifex aeolicus*. The nucleic acid and protein sequences for the I2 protein are described in, e.g., U.S. Pat. No. 6,309,643.

The level of anti-I2 antibody present in a sample from an individual can be determined using an I2 protein or a fragment thereof such as an immunoreactive fragment thereof. Suitable I2 antigens useful in determining anti-I2 antibody levels in a sample include, without limitation, an I2 protein, an I2 polypeptide having substantially the same amino acid sequence as the I2 protein, or a fragment thereof such as an immunoreactive fragment thereof. Such I2 polypeptides exhibit greater sequence similarity to the I2 protein than to the *C. pasteurianum* protein 4 and include isotype variants and homologs thereof. As used herein, an I2 polypeptide generally describes polypeptides having an amino acid sequence with greater than about 50% identity, preferably greater than about 60% identity, more preferably greater than about 70% identity, still more preferably greater than about 80%, 85%, 90%, 95%, 96%, 97%, 98%, or 99% amino acid sequence identity with a naturally-occurring I2 protein, with the amino acid identity determined using a sequence alignment program such as CLUSTALW. Such I2 antigens can be prepared, for example, by purification from microbes, by recombinant expression of a nucleic acid encoding an I2 antigen, by synthetic means such as solution or solid phase peptide synthesis, or by using phage display. Determination of anti-I2 antibody levels in a sample can be done by a histological assay or an ELISA assay as described in, e.g., U.S. Pat. No. 7,873,479.

In certain embodiments, the anti-microbial antibody biomarker is a binary rather than a numerical variable since its value is either positive or negative. For example, the value may be positive if it is above a cutoff value (e.g., above a Q3 cutoff value) and negative if it is below a cutoff value (e.g., below a Q3 cutoff value). In some embodiments, an anti-microbial antibody-positive status is associated with a higher risk of endoscopic, histological, or clinical recurrence.

Inflammatory Markers

Non-limiting examples of inflammatory markers include cytokines, chemokines, acute phase proteins, cellular adhesion molecules, S100 proteins, and combinations thereof. In certain instances, the inflammatory markers include, but are not limited to, TNF-α, IL-12p70, IL-1β, IL-2, IL-6, IL8, SDF-1, GM-CSF, IL-13, IFN-γ, SAA, CRP, ICAM, VCAM, TWEAK, and combinations thereof.

a) Cytokines

The determination of the presence or level of at least one cytokine or chemokine in a sample can be useful in the methods of the invention. As used herein, the term "cytokine" includes any of a variety of polypeptides or proteins secreted by immune cells that regulate a range of immune system functions and encompasses small cytokines such as chemokines. The term "cytokine" also includes adipocytokines, which comprise a group of cytokines secreted by adipocytes that function, e.g., in the regulation of body weight, hematopoiesis, angiogenesis, wound healing, insulin resistance, the immune response, and the inflammatory response.

In certain embodiments, the presence or level of at least one cytokine including, but not limited to, granulocyte-macrophage colony-stimulating factor (GM-CSF), IFN-γ, IL-1β, IL-2, IL-6, IL-8, TNF-α, soluble tumor necrosis factor-α receptor II (sTNF RII), TNF-related weak inducer of apoptosis (TWEAK), osteoprotegerin (OPG), IFN-α, IFN-β, IL-1α, IL-1 receptor antagonist (IL-1ra), IL-4, IL-5, soluble IL-6 receptor (sIL-6R), IL-7, IL-9, IL-12 (e.g., IL-12p70), IL-13, IL-15, IL-17, IL-23, and IL-27 is measured in a sample.

In certain other embodiments, the presence or level of at least one chemokine including, but not limited to, CXCL1/GRO1/GROα, CXCL2/GRO2, CXCL3/GRO3, CXCL4/PF-4, CXCL5/ENA-78, CXCL6/GCP-2, CXCL7/NAP-2, CXCL9/MIG, CXCL10/IP-10, CXCL11/I-TAC, CXCL12/SDF-1, CXCL13/BCA-1, CXCL14/BRAK, CXCL15, CXCL16, CXCL17/DMC, CCL1, CCL2/MCP-1, CCL3/MIP-1α, CCL4/MIP-1β, CCL5/RANTES, CCL6/C10, CCL7/MCP-3, CCL8/MCP-2, CCL9/CCL10, CCL11/Eotaxin, CCL12/MCP-5, CCL13/MCP-4, CCL14/HCC-1, CCL15/MIP-5, CCL16/LEC, CCL17/TARC, CCL18/MIP-4, CCL19/MIP-3β, CCL20/MIP-3α, CCL21/SLC, CCL22/MDC, CCL23/MPIF1, CCL24/Eotaxin-2, CCL25/TECK, CCL26/Eotaxin-3, CCL27/CTACK, CCL28/MEC, CL1, CL2, and $CX_3CL1$ is measured in a sample. In further embodiments, the presence or level of at least one adipocytokine including, but not limited to, leptin, adiponectin, resistin, active or total plasminogen activator inhibitor-1 (PAI-1), visfatin, and retinol binding protein 4 (RBP4) is measured in a sample. In particular embodiments, the presence or level of at least one of SDF-1, GM-CSF, IFN-γ, IL-1β, IL-2, IL-6, IL-8, TNF-α, sTNF RII, and/or other cytokines or chemokines is measured.

Suitable ELISA kits for determining the presence or level of a cytokine or chemokine of interest in a serum, plasma, saliva, or urine sample are available from, e.g., R&D Systems, Inc. (Minneapolis, Minn.), Neogen Corp. (Lexington, Ky.), Alpco Diagnostics (Salem, N.H.), Assay Designs, Inc. (Ann Arbor, Mich.), BD Biosciences Pharmingen (San Diego, Calif.), Invitrogen (Camarillo, Calif.), Calbiochem (San Diego, Calif.), CHEMICON International, Inc. (Temecula, Calif.), Antigenix America Inc. (Huntington Station, N.Y.), QIAGEN Inc. (Valencia, Calif.), Bio-Rad Laboratories, Inc. (Hercules, Calif.), and/or Bender MedSystems Inc. (Burlingame, Calif.).

The human IL-1β polypeptide sequence is set forth in, e.g., Genbank Accession No. NP_000567. The human IL-1β mRNA (coding) sequence is set forth in, e.g., Genbank Accession No. NM_000576. One skilled in the art will appreciate that IL-1β is also known as IL1F2 and IL-1beta.

The human IL-2 polypeptide sequence is set forth in, e.g., Genbank Accession No. NP_000577. The human IL-2 mRNA (coding) sequence is set forth in, e.g., Genbank Accession No. NM_000586. One skilled in the art will appreciate that IL-2 is also known as TCGF and lymphokine.

The human IL-6 polypeptide sequence is set forth in, e.g., Genbank Accession No. NP_000591. The human IL-6 mRNA (coding) sequence is set forth in, e.g., Genbank Accession No. NM_000600. One skilled in the art will appreciate that IL-6 is also known as interferon beta 2 (IFNB2), HGF, HSF, and BSF2.

The human IL-8 polypeptide sequence is set forth in, e.g., Genbank Accession No. NP_000575. The human IL-8 mRNA (coding) sequence is set forth in, e.g., Genbank Accession No. NM_000584. One skilled in the art will appreciate that IL-8 is also known as CXCL8, K60, NAF, GCP1, LECT, LUCT, NAP1, 3-10C, GCP-1, LYNAP, MDNCF, MONAP, NAP-1, SCYB8, TSG-1, AMCF-I, and b-ENAP.

The human GM-CSF polypeptide sequence is set forth in, e.g., Genbank Accession No. NP_000749. The human GM-CSF mRNA (coding) sequence is set forth in, e.g., Genbank Accession No. NM_000758. One skilled in the art will appreciate that GM-CSF is also known as granulocyte-macrophage colony stimulating factor, colony stimulating factor 2 (granulocyte-macrophage), GSF2 and GMCSF.

The human IFNγ polypeptide sequence is set forth in, e.g., Genbank Accession No. NP_000610. The human IFNγ mRNA (coding) sequence is set forth in, e.g., Genbank Accession No. NM_000619. One skilled in the art will appreciate that GM-CSF is also known as interferon gamma, IFNG, IFG, IFI, and IFN gamma.

The human TNFα polypeptide sequence is set forth in, e.g., Genbank Accession No. NP_000585. The human TNFα mRNA (coding) sequence is set forth in, e.g., Genbank Accession No. NM_000594. One skilled in the art will appreciate that TNFα is also known as tumor necrosis factor, TNF, DIF, TNF-alpha, TNFA, and TNFSF2.

The human TNF-related weak inducer of apoptosis (TWEAK) polypeptide sequence is set forth in, e.g., Genbank Accession No. NP_003800.1. The human TWEAK mRNA (coding) sequence is set forth in, e.g., Genbank Accession No. NM_003809.2. One skilled in the art will appreciate that TWEAK is also known as TNF12, APO3 ligand, APO3L, DR3LG, and UNQ181/PRO207.

The human IL-12p70 polypeptide is a heterodimer made up of two subunits of IL-12 proteins: one is 40 kDa (IL-12p40) and one is 35 kDa (IL-12p35). Suitable ELISA kits for determining the presence or level of IL-12p70 in a serum, plasma, saliva, or urine sample are available from, e.g., Gen-Probe Diaclone SAS (France), Abazyme (Needham, Mass.), BD Biosciences Pharmingen (San Diego, Calif.), Cell Sciences (Canton, Mass.), eBioscience (San Diego, Calif.), Invitrogen (Camarillo, Calif.), R&D Systems, Inc. (Minneapolis, Minn.), and Thermo Scientific Pierce Protein Research Products (Rockford, Ill.).

b) Acute Phase Proteins

The determination of the presence or level of one or more acute phase proteins in a sample can also be useful in the methods of the invention. Acute-phase proteins are a class of proteins whose plasma concentrations increase (positive acute-phase proteins) or decrease (negative acute-phase proteins) in response to inflammation. This response is called the acute-phase reaction (also called acute-phase response). Examples of positive acute-phase proteins include, but are not limited to, C-reactive protein (CRP), D-dimer protein, mannose-binding protein, alpha 1-antitrypsin, alpha 1-antichymotrypsin, alpha 2-macroglobulin, fibrinogen, prothrombin, factor VIII, von Willebrand factor, plasminogen, complement factors, ferritin, serum amyloid P component, serum amyloid A (SAA), orosomucoid (alpha 1-acid glycoprotein, AGP), ceruloplasmin, haptoglobin, and combinations thereof. Non-limiting examples of negative acute-phase proteins include albumin, transferrin, transthyretin, transcortin, retinol-binding protein, and combinations thereof. In particular embodiments, the presence or level of CRP and/or SAA is determined.

In certain instances, a sandwich colorimetric ELISA assay available from Alpco Diagnostics (Salem, N.H.) can be used to measure the level of CRP in a serum, plasma, urine, or stool sample. Similarly, an ELISA kit available from Biomeda Corporation (Foster City, Calif.) can be used to detect CRP levels in a sample. Other methods for measuring CRP levels in a sample are described in, e.g., U.S. Pat. Nos. 6,838,250; 6,406,862; 7,439,019; and U.S. Patent Publication No. 20060019410. Additional methods for measuring CRP levels include, e.g., immunoturbidimetry assays, rapid immunodiffusion assays, and visual agglutination assays. Suitable ELISA kits for detecting the presence or level of SAA in a sample such as a serum, plasma, saliva, urine, or stool sample are available from, e.g., Antigenix America Inc. (Huntington Station, N.Y.), Abazyme (Needham, Mass.), USCN Life (Missouri City, Tex.), and U.S. Biological (Swampscott, Mass.).

C-reactive protein (CRP) is a protein found in the blood in response to inflammation (an acute-phase protein). CRP is typically produced by the liver and by fat cells (adipocytes). It is a member of the pentraxin family of proteins. The human CRP polypeptide sequence is set forth in, e.g., Genbank Accession No. NP_000558. The human CRP mRNA (coding) sequence is set forth in, e.g., Genbank Accession No. NM_000567. One skilled in the art will appreciate that CRP is also known as PTX1, MGC88244, and MGC149895.

In certain embodiments, the acute phase protein biomarker is a binary rather than a numerical variable since its value is either positive or negative. For example, the value may be positive if it is above a cutoff value (e.g., above about 5 mg/L) and negative if it is below a cutoff value (e.g., below about 5 mg/L). In some embodiments, an acute phase protein-positive status is associated with a higher risk of endoscopic, histological, or clinical recurrence.

Serum amyloid A (SAA) proteins are a family of apolipoproteins associated with high-density lipoprotein (HDL) in plasma. Different isoforms of SAA are expressed constitutively (constitutive SAAs) at different levels or in response to inflammatory stimuli (acute phase SAAs). These proteins are predominantly produced by the liver. The conservation of these proteins throughout invertebrates and vertebrates suggests SAAs play a highly essential role in all animals. Acute phase serum amyloid A proteins (A-SAAs) are secreted during the acute phase of inflammation. The human SAA polypeptide sequence is set forth in, e.g., Genbank Accession No. NP_000322. The human SAA mRNA (coding) sequence is set forth in, e.g., Genbank Accession No. NM_000331. One skilled in the art will appreciate that SAA is also known as PIG4, TP53I4, MGC111216, and SAA1.

c) Immunoglobulin Proteins

The determination of the presence or level of one or more immunoglobulin superfamily cellular adhesion molecules in a sample can also be useful in the methods of the invention. As used herein, the term "immunoglobulin superfamily cellular adhesion molecule" (IgSF CAM) includes any of a variety of polypeptides or proteins located on the surface of a cell that have one or more immunoglobulin-like fold domains, and which function in intercellular adhesion and/or signal transduction. In many cases, IgSF CAMs are transmembrane proteins. Non-limiting examples of IgSF CAMs include Neural Cell Adhesion Molecules (NCAMs; e.g., NCAM-120, NCAM-125, NCAM-140, NCAM-145, NCAM-180, NCAM-185, etc.), Intercellular Adhesion Molecules (ICAMs, e.g., ICAM-1, ICAM-2, ICAM-3, ICAM-4, and ICAM-5), Vascular Cell Adhesion Molecule-1 (VCAM-1), Platelet-Endothelial Cell Adhesion Molecule-1 (PECAM-1), L1 Cell Adhesion Molecule (L1CAM), cell adhesion molecule with homology to L1CAM (close homolog of L1) (CHL1), sialic acid binding Ig-like lectins (SIGLECs; e.g., SIGLEC-1, SIGLEC-2, SIGLEC-3, SIGLEC-4, etc.), Nectins (e.g., Nectin-1, Nectin-2, Nectin-3, etc.), and Nectin-like molecules (e.g., Necl-1, Necl-2, Necl-3, Necl-4, and Necl-5). In particular embodiments, the presence or level of ICAM-1 and/or VCAM-1 is determined.

ICAM-1 (ICAM) is a transmembrane cellular adhesion protein that is continuously present in low concentrations in the membranes of leukocytes and endothelial cells. Upon cytokine stimulation, the concentrations greatly increase. ICAM-1 can be induced by IL-1 and TNFα and is expressed by the vascular endothelium, macrophages, and lymphocytes. In IBD, proinflammatory cytokines cause inflammation by upregulating expression of adhesion molecules such as ICAM-1 and VCAM-1. The increased expression of adhesion molecules recruit more lymphocytes to the infected tissue, resulting in tissue inflammation (see, Goke et al., *J., Gastroenterol.*, 32:480 (1997); and Rijcken et al., *Gut*, 51:529 (2002)). ICAM-1 is encoded by the intercellular adhesion molecule 1 gene (ICAM1; Entrez GeneID:3383; Genbank Accession No. NM_000201) and is produced after processing of the intercellular adhesion molecule 1 precursor polypeptide (Genbank Accession No. NP_000192).

VCAM-1 (VCAM) is a transmembrane cellular adhesion protein that mediates the adhesion of lymphocytes, monocytes, eosinophils, and basophils to vascular endothelium. Upregulation of VCAM-1 in endothelial cells by cytokines occurs as a result of increased gene transcription (e.g., in response to tumor necrosis factor-alpha (TNFα) and Interleukin-1 (IL-1)). VCAM-1 is encoded by the vascular cell adhesion molecule 1 gene (VCAM1; Entrez GeneID:7412) and is produced after differential splicing of the transcript (Genbank Accession No. NM_001078 (variant 1) or NM_080682 (variant 2)), and processing of the precursor polypeptide splice isoform (Genbank Accession No. NP_001069 (isoform a) or NP_542413 (isoform b))).

Suitable antibodies and/or ELISA kits for detecting the presence or level of ICAM-1 and/or VCAM-1 in a sample such as a tissue sample, biopsy, serum, plasma, saliva, urine, or stool are available from, e.g., Invitrogen (Camarillo, Calif.), Santa Cruz Biotechnology, Inc. (Santa Cruz, Calif.), and/or Abcam Inc. (Cambridge, Mass.).

Drug Analytes

In some embodiments, the method comprises determining the presence and/or level of a drug analyte in a sample (e.g., a serum sample from a subject on anti-TNFα drug therapy). In certain instances, the measurements can be made at multiple time points, e.g., before, during, and/or after the course of therapy. In some embodiments, the drug analyte is a biologic drug (e.g., an anti-TNFα drug) and/or an anti-drug antibody (ADA) (e.g., the level of autoantibody to a biologic drug such as human anti-chimeric antibody (HACA), human anti-humanized antibody (HAHA), and human anti-mouse antibody (HAMA), and combinations thereof).

In certain embodiments, the method of detecting an anti-drug antibody includes determining the presence or level of anti-drug antibody (ADA) isotypes in ADA-positive patients receiving biologic therapy. Non-limiting examples of antibody isotypes include IgA, IgD, IgE, IgG, and IgM.

In particular embodiments, the presence or level of a biologic drug (e.g., an anti-TNFα drug) and/or ADA is determined with a homogeneous mobility shift assay (HMSA) using size exclusion chromatography. These methods and related technology are described in PCT Patent Publication Nos. WO 2011/056590, WO 2012/054532, WO 2012/154253 and WO 2013/006810, and U.S. Provisional Application No. 61/683,681, filed Aug. 15, 2012, the disclosures of which are incorporated by reference in their entirety for all purposes.

Non-limiting examples of other methods for determining the presence or level of a drug analyte (e.g., a biologic and/or ADA) include enzyme-linked immunosorbent assays (ELISAs) such as bridging ELISAs. For example, the Infliximab ELISA from Matriks Biotek Laboratories detects free infliximab in serum and plasma samples, and the HACA ELISA from PeaceHealth Laboratories detects HACA in serum samples.

IV. Statistical Methods

In some aspects, one or more statistical algorithms such as, e.g, learning statistical classifier systems are applied to the presence, absence, and/or level of one or more serological markers determined by any of the assays described herein to predict endoscopic, histological, or clinical recurrence. In some aspects, one or more statistical algorithms are applied to the presence, absence, or level of one or more serological markers and/or clinical markers to predict endoscopic, histological, or clinical recurrence.

The term "statistical analysis" or "statistical algorithm" or "statistical process" includes any of a variety of statistical methods and models used to determine relationships between variables. In the present invention, the variables are the presence, absence, or level of at least one marker (e.g., serological or clinical) of interest. Any number of markers can be analyzed using a statistical analysis described herein. For example, the presence, absence, or level of 1, 2, 3, 4, 5, 6, 7, 8, 9, 10, 11, 12, 13, 14, 15, 16, 17, 18, 19, 20, 25, 30, 35, 40, 45, 50, 55, 60, or more markers can be included in a statistical analysis. In one embodiment, logistic regression is used. In another embodiment, linear regression is used. In a further embodiment, a Cox proportional hazards regression model is used.

In certain embodiments, the statistical analyses of the present invention comprise a quantile measurement of one or more markers, e.g., within a given population, as a variable. Quantiles are a set of "cut points" that divide a sample of data into groups containing (as far as possible) equal numbers of observations. For example, quartiles are values that divide a sample of data into four groups containing (as far as possible) equal numbers of observations. The lower quartile is the data value a quarter of the way up through the ordered data set; the upper quartile is the data value a quarter of the way down through the ordered data set. Quintiles are values that divide a sample of data into five groups containing (as far as possible) equal numbers of observations. The present invention can also include the use of percentile ranges of marker levels (e.g., tertiles, quartile, quintiles, etc.), or their cumulative indices (e.g., quartile sums of marker levels to obtain quartile sum scores (QSS), etc.) as variables in the statistical analyses (just as with continuous variables).

In particular embodiments, the statistical analysis comprises one or more learning statistical classifier systems. As used herein, the term "learning statistical classifier system" includes a machine learning algorithmic technique capable of adapting to complex data sets (e.g., panel of markers of interest) and making decisions based upon such data sets. In some embodiments, a single learning statistical classifier system such as a decision/classification tree (e.g., random forest (RF) or classification and regression tree (C&RT)) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naïve learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ).

Random forests are learning statistical classifier systems that are constructed using an algorithm developed by Leo Breiman and Adele Cutler. Random forests use a large number of individual decision trees and decide the class by choosing the mode (i.e., most frequently occurring) of the classes as determined by the individual trees. Random forest analysis can be performed, e.g., using the RandomForests software available from Salford Systems (San Diego, Calif.). See, e.g., Breiman, *Machine Learning,* 45:5-32 (2001).

Classification and regression trees represent a computer intensive alternative to fitting classical regression models and are typically used to determine the best possible model for a categorical or continuous response of interest based upon one or more predictors. Classification and regression tree analysis can be performed, e.g., using the C&RT software available from Salford Systems or the Statistica data analysis software available from StatSoft, Inc. (Tulsa, Okla.). A description of classification and regression trees is found, e.g., in Breiman et al. "Classification and Regression Trees," Chapman and Hall, New York (1984); and Steinberg et al., "CART: Tree-Structured Non-Parametric Data Analysis," Salford Systems, San Diego, (1995).

Neural networks are interconnected groups of artificial neurons that use a mathematical or computational model for information processing based on a connectionist approach to computation. Typically, neural networks are adaptive systems that change their structure based on external or internal information that flows through the network. Specific examples of neural networks include feed-forward neural networks such as perceptrons, single-layer perceptrons, multi-layer perceptrons, backpropagation networks, ADALINE networks, MADALINE networks, Learnmatrix networks, radial basis function (RBF) networks, and self-organizing maps or Kohonen self-organizing networks; recurrent neural networks such as simple recurrent networks and Hopfield networks; stochastic neural networks such as Boltzmann machines; modular neural networks such as committee of machines and associative neural networks; and other types of networks such as instantaneously trained neural networks, spiking neural networks, dynamic neural networks, and cascading neural networks. Neural network analysis can be performed, e.g., using the Statistica data analysis software available from StatSoft, Inc. See, e.g., Freeman et al., In "Neural Networks: Algorithms, Applications and Programming Techniques," Addison-Wesley Publishing Company (1991); Zadeh, Information and Control, 8:338-353 (1965); Zadeh, "IEEE Trans. on Systems, Man and Cybernetics," 3:28-44 (1973); Gersho et al., In "Vector Quantization and Signal Compression," Kluywer Academic Publishers, Boston, Dordrecht, London (1992); and Hassoun, "Fundamentals of Artificial Neural Networks," MIT Press, Cambridge, Mass., London (1995), for a description of neural networks.

Support vector machines are a set of related supervised learning techniques used for classification and regression and are described, e.g., in Cristianini et al., "An Introduction to Support Vector Machines and Other Kernel-Based Learning Methods," Cambridge University Press (2000). Support vector machine analysis can be performed, e.g., using the SVM$^{light}$ software developed by Thorsten Joachims (Cornell University) or using the LIBSVM software developed by Chih-Chung Chang and Chih-Jen Lin (National Taiwan University).

The various statistical methods and models described herein can be trained and tested using a cohort of samples (e.g., serological samples) from individuals that exhibit post-operative recurrence and patients that do not experience post-operative recurrence within a given time interval (e.g., at least about 1, 2, 3, 4, 5, 6, 7, 8, 9, 10, 11, or 12 months; or at least about 1, 2, 3, 4, or 5 years). Samples from patients experiencing post-operative CD recurrence can also be stratified into patients experiencing endoscopic, histological, radiographic, or clinical recurrence. One skilled in the art will know of additional techniques and diagnostic criteria for obtaining a cohort of patient samples that can be used in training and testing the statistical methods and models of the present invention.

As used herein, the term "sensitivity" refers to the probability that a method of the present invention gives a positive result when the sample is positive. Sensitivity is calculated as the number of true positive results divided by the sum of the true positives and false negatives. In certain instances, sensitivity is a measure of how well the present invention correctly predicts those patients who will experience post-operative recurrence (e.g., post-operative endoscopic, radiographic, clinical, or histological recurrence). The statistical methods and models can be selected such that the sensitivity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "specificity" refers to the probability that a method of the invention gives a negative result when the sample is not positive. Specificity is calculated as the number of true negative results divided by the sum of the true negatives and false positives. In certain instances, specificity is a measure of how well the present invention excludes those who will not experience post-operative CD recurrence (e.g., post-operative endoscopic, radiographic, clinical, or histological recurrence) from those who will experience post-operative CD recurrence. The statistical methods and models can be selected such that the specificity is at least about 60%, and can be, e.g., at least about 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

The term "negative predictive value" or "NPV" refers to the probability that an individual predicted not to experience post-operative CD recurrence (e.g., post-operative endoscopic, radiographic, clinical, or histological recurrence) actually does experience post-operative CD recurrence. Negative predictive value can be calculated as the number of true negatives divided by the sum of the true negatives and false negatives. Negative predictive value is determined by the characteristics of the method as well as the frequency of recurrence in the population analyzed. The statistical methods and models can be selected such that the negative predictive value in a population of post-operative CD patients is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

As used herein, the term "positive predictive value" or "PPV" refers to the probability that an individual predicted to experience post-operative CD recurrence (e.g., post-operative endoscopic, radiographic, clinical, or histological recurrence) actually experiences post-operative CD recurrence. Positive predictive value can be calculated as the number of true positives divided by the sum of the true positives and false positives. Positive predictive value is determined by the characteristics of the method as well as the prevalence of the disease in the population analyzed. The statistical methods and models can be selected such that the positive predictive value in a population having a disease prevalence is in the range of about 70% to about 99% and can be, for example, at least about 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Predictive values, including negative and positive predictive values, are influenced by the frequency of recurrence in the population analyzed. In the present invention, the statistical methods and models can be selected to produce a desired clinical parameter for a clinical population with a particular frequency of post-operative CD recurrence (e.g., post-operative endoscopic, radiographic, clinical, or histological recurrence). For example, statistical methods and models can be selected for a frequency of post-operative CD recurrence of up to about 1%, 2%, 3%, 4%, 5%, 6%, 7%, 8%, 9%, 10%, 15%, 20%, 25%, 30%, 35%, 40%, 45%, 50%, 55%, 60%, 65%, or 70%.

As used herein, the term "overall agreement" or "overall accuracy" refers to the accuracy with which a method of the present invention identifies those who will experience post-operative recurrence (e.g., post-operative endoscopic, radiographic, clinical, or histological recurrence). Overall accuracy is calculated as the sum of the true positives and true negatives divided by the total number of sample results and is affected by the frequency of post-operative CD recurrence in the population analyzed. For example, the statistical methods and models of the invention can be selected such that the overall accuracy in a patient population having a particular frequency of post-operative CD recurrence is at least about 40%, and can be, e.g., at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, patients are predicted to experience post-operative CD recurrence (e.g., post-operative endoscopic, radiographic, clinical, or histological recurrence) by calculating or applying an odds ratio (OR). An OR is a measure of association between a presence, absence, or level of a marker and an outcome. The OR represents the odds that post-operative CD recurrence will occur given the presence, absence, or level of the marker (e.g., a clinical or serological marker). In some embodiments, an OR is calculated using logistic regression. In some cases, the logistic regression model is used to calculate an OR between a binary predictive variable (e.g., presence or absence of one or more markers) and a binary dependent variable (e.g., post-operative CD recurrence). An OR of 1 means that the marker does not predict the odds of post-operative CD recurrence. An OR of less than 1 means that the marker is associated with lower odds of post-operative CD recurrence. An OR of greater than 1 means that the marker is associated with greater odds of post-operative CD recurrence. An OR can be provided with a confidence interval. The confidence interval provides an estimate of the precision of the OR. A large confidence interval indicates a lower OR precision, while a small confidence interval indicates an OR with a high precision. A p-value indicates whether the OR is statistically significant.

In some embodiments, the presence, absence, or level of markers with an OR above 1, including but not limited to one or more of anti-FlaX, anti-CBir1, anti-Fla2, pANCA, and whether the patient is an active smoker, are used to predict the likelihood of post-operative CD recurrence. In some embodiments, the presence, or absence, of markers above a Q3 cutoff value that are calculated to have an OR above 1, including but not limited to one or more of anti-FlaX, anti-CBir1, anti-Fla2, pANCA, and whether the patient is an active smoker, are used to predict the likelihood of post-operative CD recurrence.

In some embodiments, patients are predicted to experience post-operative CD recurrence (e.g., post-operative endoscopic, radiographic, clinical, or histological recurrence) by calculating or applying a hazard ratio (HR). In certain embodiments, the HR is calculated using a Cox Proportional Hazard Model. The Cox model provides an estimate of the hazard ratio and its confidence interval. The confidence interval provides an estimate of the precision of the HR. A large confidence interval indicates a lower HR precision, while a small confidence interval indicates an HR with a high precision. A p-value indicates whether the HR is statistically significant. In some embodiments, the HR is a measure of how often post-operative CD recurrence happens in one group, defined by a presence, absence, or level of one or more markers, compared to how often it happens in another group, defined by a different presence, absence, or level of one or more markers, over time. A hazard ratio of one means that there is no difference in post-operative CD recurrence between the two groups. A hazard ratio of greater or less than one means that the frequency of post-operative CD recurrence was lower in one of the groups.

In some embodiments, the presence, absence, or level of one or more markers with an HR above 1, including but not limited to one or more of anti-FlaX, anti-CBir1, anti-Fla2, pANCA, and whether the patient is an active smoker, are used to predict the likelihood of post-operative CD recurrence. In some embodiments, the presence, or absence, of one or more markers above a Q3 cutoff value that are calculated to have an HR above 1, including but not limited to one or more of anti-FlaX, anti-CBir1, anti-Fla2, pANCA, and whether the patient is an active smoker, are used to predict the likelihood of post-operative CD recurrence.

V. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1. Serological Markers Predictive of Post-Operative Endoscopic Histological and Clinical Recurrence of Crohn's Disease This example illustrates a method of utilizing a panel of serological markers in CD patients collected prior to right hemicolectomy to predict post-operative endoscopic, histological, or clinical recurrence.

Background

A majority of Crohn's disease (CD) patients will require a partial bowel resection during their disease course. Most of these patients will experience a postoperative recurrence of the disease. Endoscopy, histology, or radiography within the first year after surgery can reveal new epithelial lesions. The severity of these lesions predicts the recurrence of clinical symptoms and the need for additional surgical intervention.

Since endoscopy, radiology, and histology are a burden to the post-operative patient, predictors of recurrence are warranted. A wide range of clinical and histological features have been identified. However, literature often provides conflicting data, partially due to variable definitions of CD recurrence and methodological discrepancies such as the length and type of follow up. Serological markers have been associated with more complicated and aggressive CD behavior. Furthermore, development of a complicated disease phenotype and CD-related abdominal surgery was not only seen more frequently in patients with a higher cumulative number of positive antibodies, but also in patients with higher antibody responses towards different sets of serological markers.

Methods

The study population consisted of a consecutive cohort of 100 consecutive patients (male 41, median age 41.7 years) undergoing a right hemicolectomy for refractory CD, in whom a serum sample was collected ≤1 week prior to surgery. The surgeries were performed at the University Hospitals Leuven (Leuven, Belgium). All patients underwent post-operative endoscopic evaluation six months after surgery. Endoscopic recurrence is defined as a post-operative Rutgeerts' score of i3 or i4 (Rutgeerts et al., *Gastroenterology*, 99(4):956-63 (1990)). Data on endoscopic, clinical and surgical recurrence were collected prospectively.

Figure 2:
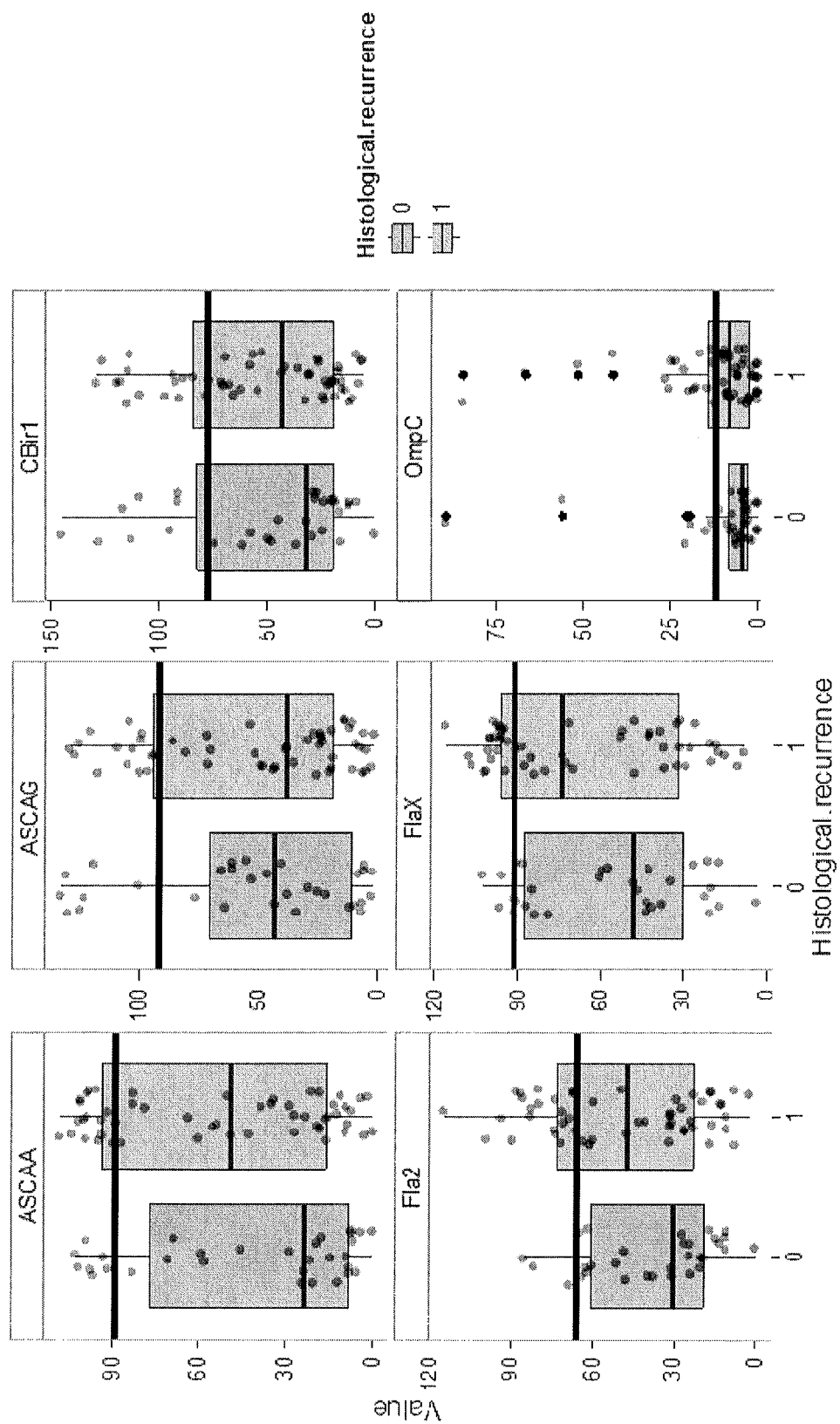
FIG. 2 depicts a boxplot comparing the indicated marker levels and whether the patient experienced clinical recurrence at 6 months.

Serum samples were taken prior to surgery and tested for serological markers ASCA-IgA, ASCA-IgG, anti-CBir1, anti-OmpC, anti-Fla2, anti-FlaX and pANCA. The marker values were separated between samples from patients exhibiting endoscopic recurrence and patients that did not exhibit endoscopic recurrence. The distribution of marker values for the endoscopic recurrence and non-recurrence patient cohorts is depicted in FIG. 1. The marker values were also separated between samples from patients exhibiting histological recurrence and patients that did not exhibit histological recurrence. The distribution of marker values for the histological recurrence and non-recurrence patient cohorts is depicted in FIG. 2.

Each marker's third quartile value for this data was set as a cutoff point; markers were deemed positive if they were above this cut-point. The cutoff point is provided in Table 1.

TABLE 1

Q3 Values Used as a Cutoff Point for each Marker

| Marker | ASCAA | ASCAG | anti-CBir1 | anti-Fla2 | anti-FlaX | anti-OmpC |
|---|---|---|---|---|---|---|
| Q3 | 89.17 | 91.84 | 77.87 | 65.55 | 91.48 | 12.06 |

The odds ratios, p-values from Fisher's Exact statistical tests, counts of true positives (TP), true negatives (TN), false positives (FP), and false negatives (FN), sensitivity and specificity of the binary markers for predicting endoscopic, histological, and clinical recurrence were evaluated. These values are provided for each marker in Table 2.

TABLE 2

Sensitivity and Specificity at Q3 Cutoff (underlined values are predictive of recurrence)

| Marker | Fishers Exact Test OR | Fishers Exact Test P | TP | TN | FP | FN | Sensitivity | Specificity |
|---|---|---|---|---|---|---|---|---|
| Endoscopic Recurrence | | | | | | | | |
| ASCAA | 0.896 | 1.000 | 6 | 51 | 19 | 18 | 0.250 | 0.729 |
| ASCAG | 0.188 | 0.030 | 2 | 47 | 23 | 22 | 0.083 | 0.671 |
| anti-CBir1 | 1.187 | 0.791 | 7 | 52 | 18 | 17 | 0.292 | 0.743 |
| anti-Fla2 | 3.060 | 0.033 | 11 | 55 | 15 | 13 | 0.458 | 0.786 |
| anti-FlaX | 3.060 | 0.033 | 11 | 55 | 15 | 13 | 0.458 | 0.786 |
| anti-OmpC | 1.439 | 0.597 | 8 | 52 | 18 | 16 | 0.333 | 0.743 |
| pANCA | 3.172 | 0.041 | 9 | 59 | 11 | 15 | 0.375 | 0.843 |
| Histological Recurrence | | | | | | | | |
| ASCAA | 1.476 | 0.613 | 16 | 24 | 7 | 37 | 0.302 | 0.774 |
| ASCAG | 1.349 | 0.617 | 15 | 24 | 7 | 38 | 0.283 | 0.774 |
| anti-CBir1 | 1.133 | 1.000 | 15 | 23 | 8 | 38 | 0.283 | 0.742 |
| anti-Fla2 | 6.007 | 0.005 | 21 | 28 | 3 | 32 | 0.396 | 0.903 |
| anti-FlaX | 4.028 | 0.023 | 20 | 27 | 4 | 33 | 0.377 | 0.871 |
| anti-OmpC | 1.952 | 0.311 | 17 | 25 | 6 | 36 | 0.321 | 0.806 |
| pANCA | 1.217 | 0.789 | 12 | 25 | 6 | 41 | 0.226 | 0.806 |
| Clinical Recurrence | | | | | | | | |
| ASCAA | 1.053 | 1.000 | 8 | 47 | 17 | 21 | 0.276 | 0.734 |
| ASCAG | 0.462 | 0.209 | 5 | 44 | 20 | 24 | 0.172 | 0.688 |
| anti-CBir1 | 0.815 | 0.803 | 7 | 46 | 18 | 22 | 0.241 | 0.719 |
| anti-Fla2 | 2.494 | 0.080 | 12 | 50 | 14 | 17 | 0.414 | 0.781 |
| anti-FlaX | 1.981 | 0.212 | 11 | 49 | 15 | 18 | 0.379 | 0.766 |
| anti-OmpC | 1.241 | 0.803 | 9 | 47 | 17 | 20 | 0.310 | 0.734 |
| pANCA | 3.674 | 0.014 | 11 | 55 | 9 | 18 | 0.379 | 0.859 |

Results

The results demonstrated a positive association of endoscopic recurrence with the anti-flagellin markers, anti-Fla2 and anti-FlaX (OR=3.06, p=0.033 for both) and for pANCA (OR=3.2, p=0.041). None of the other serological markers had an odds ratio significantly greater than 1.0 with endoscopic recurrence. As a predictor of endoscopic recurrence, the flagellin markers yielded a common specificity of 0.786 and a sensitivity of 0.458. pANCA had a specificity and sensitivity of 0.843 and 0.375, respectively. FLA2 and FLAX were also positively associated with histological recurrence (OR=6.0, p<0.005 and OR=4.0, p=0.023, respectively). As predictors of histological recurrence, anti-Fla2 and anti-FlaX displayed a high specificity (0.93 and 0.871, respectively) while yielding a lower sensitivity (0.396 and 0.377, respectively). The results also demonstrate that anti-Fla2 and anti-FlaX are positively associated with clinical recurrence, display a high specificity, and yield a low sensitivity.

Conclusions

Serological markers can be useful as predictors of post-operative endoscopic, clinical, and histological recurrence in Crohn's disease. If elevated flagellins are seen in pre-operative serum samples, post-op intervention or therapy may be required to reduce the risk of recurrence as suggested by Clarke et al. (Clarke et al., *Gastroenterol. & Hepatol.*, 5, 2009).

Example 2. Pre-Operative Serological Markers Predict Post-Operative Crohn's Disease Recurrence: Results from a Prospective Mono-Centric Trial This example illustrates a method of utilizing a panel of serological markers in CD patients collected prior to an intestinal resection in conjunction with a clinical marker to predict post-operative endoscopic, or clinical recurrence.

Background

Preventing postoperative endoscopic (ER) and clinical recurrence (CR) remains a challenging issue in patients with Crohn's disease (CD) undergoing an intestinal resection. Several clinical and histological risk factors have been identified, and may guide selection of appropriate candidates for postoperative prophylactic CD therapy. We evaluated if a set of pre-operative serological markers could strengthen the prediction of postoperative ER and CR.

Methods

The study population of Example 1 was utilized for further analysis. At surgery, 27 patients were active smoking and 55 had an elevated C-reactive protein level (CRP>5 mg/L). All patients were followed prospectively and underwent a postoperative endoscopic evaluation at 6 months. The primary endpoint (ER) was defined as a postoperative endoscopic recurrence score of i3 or i4. Secondary endpoints included time to clinical recurrence. Sera were analyzed blindly for the expression of anti-*Saccharomyces cerevisiae* IgA (ASCA A) and IgG antibodies (ASCA G), three different anti-flagellin antibodies (anti-CBir1, anti-Fla2, and anti-FlaX), antibodies to the outer-membrane porin C of *Escherichia coli* (anti-OmpC), and atypical perinuclear antineutrophilic cytoplasmic antibodies (pANCA). The Q3 value of each individual marker in this dataset, as defined in the previous example, was utilized as the cut-off point. Predictors of both ER and CR in univariate analyses were included in the binary logistic and Cox regression analysis.

Results

Figure 3:
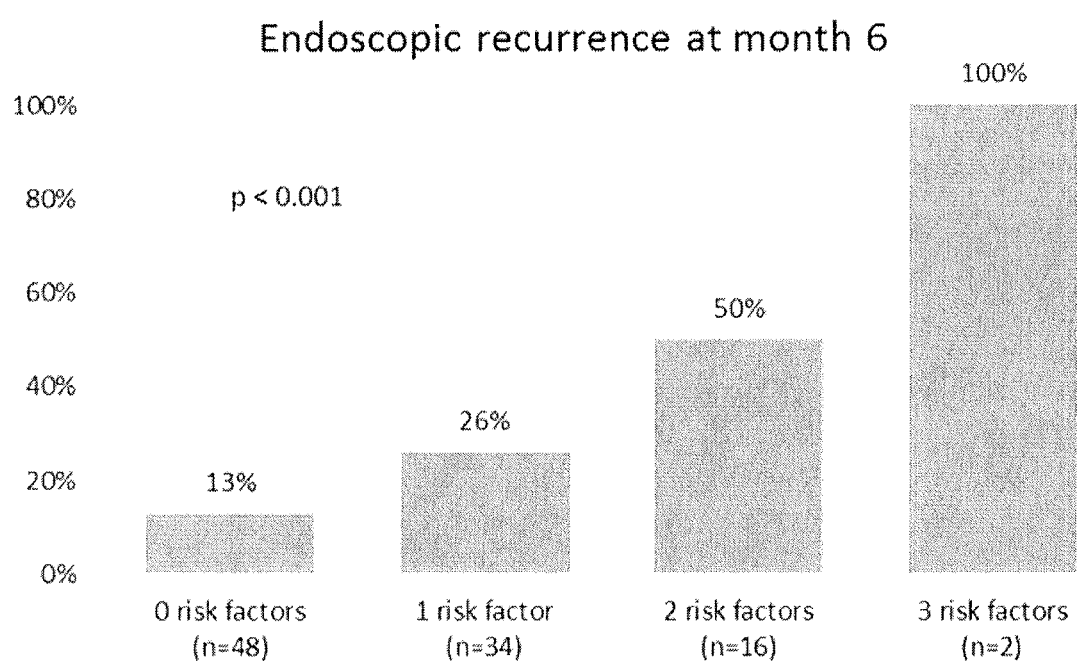
FIG. 3 depicts a chart of endoscopic recurrence with respect to the number of risk factors detected in a preoperative patient sample at 6 months after right hemicolectomy for refractory Crohn's disease.
Figure 4:
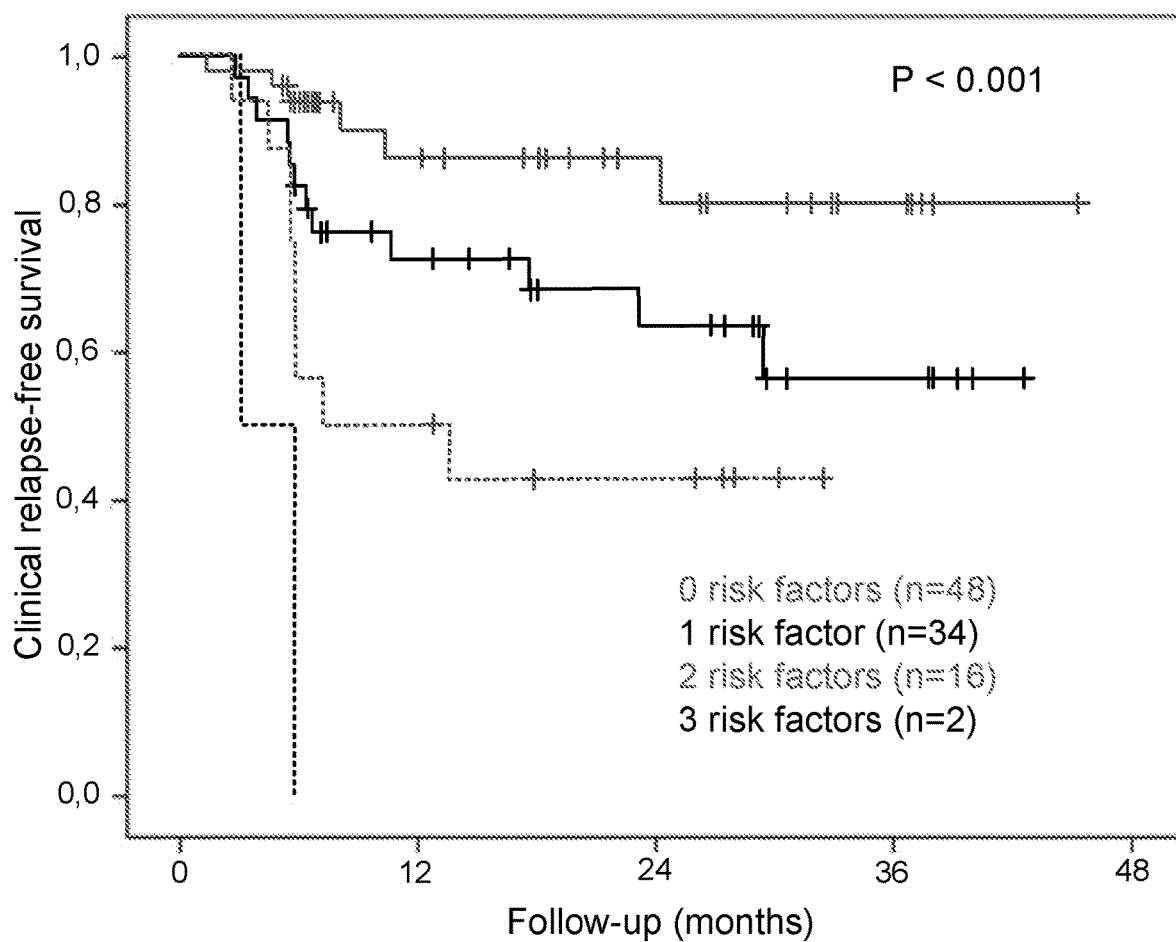
FIG. 4 depicts clinical recurrence with respect to the number of risk factors detected in a preoperative patient sample at 6 months after right hemicolectomy for refractory Crohn's disease.

Twenty-five patients developed ER at 6 months. anti-Fla2>66 EU/ml and active smoking were independently associated with ER (Table 3). During a median follow-up of 23.6 months, 29 patients developed a CR, with anti-Fla2>66 EU/ml, pANCA positivity and active smoking as independent risk factors (Table 3). A cumulative risk score was developed by combining 3 risk factors (anti-Fla2>66 EU/ml, pANCA positivity, and active smoking). Based on this cumulative risk score, we could observe a significant and gradual increased risk of both ER (FIG. 3, linear-by-linear p<0.001) and CR (FIG. 4, LogRank p<0.001).

TABLE 3

Multivariate Analysis Results

|  | Endoscopic recurrence *<br>(Logistic Regression) | Clinical recurrence **<br>(Cox Regression) |
|---|---|---|
| anti-Fla2 > 66 EU | 3.0 (1.1-8.7)<br>p = 0.037 | 2.2 (1.0-4.6)<br>p = 0.041 |
| pANCA positive | 2.7 (0.9-8.1)<br>p = 0.083 | 2.5 (1.2-5.4)<br>p = 0.016 |
| Active smoking | 3.1 (1.1-8.8)<br>p = 0.029 | 2.6 (1.2-5.5)<br>p = 0.011 |

\* Odds ratio (95% confidence interval)
\*\* Hazard ratio (95% confidence interval)

Example 3. Determination of ANCA Levels

This example illustrates an analysis of ANCA levels in a sample using an ELISA assay.

A fixed neutrophil enzyme-linked immunosorbent assay (ELISA) may be used to detect ANCA as described in Saxon et al., *J. Allergy Clin. Immunol.*, 86:202-210 (1990). Briefly, microtiter plates are coated with $2.5 \times 10^5$ neutrophils per well from peripheral human blood purified by Ficoll-hypaque centrifugation and treated with 100% methanol for 10 minutes to fix the cells. Cells are incubated with 0.25% bovine serum albumin (BSA) in phosphate-buffered saline to block nonspecific antibody binding for 60 minutes at room temperature in a humidified chamber. Next, control and coded sera are added at a 1:100 dilution to the bovine serum/phosphate-buffered saline blocking buffer and incubated for 60 minutes at room temperature in a humidified chamber. Alkaline phosphatase-conjugated goat F(ab')$_2$ anti-human immunoglobulin G antibody (γ-chain specific; Jackson Immunoresearch Labs, Inc.; West Grove, Pa.) is added at a 1:1000 dilution to label neutrophil-bound antibody and incubated for 60 minutes at room temperature. A solution of p-nitrophenol phosphate substrate is added, and color development is allowed to proceed until absorbance at 405 nm in the positive control wells is 0.8-1.0 optical density units greater than the absorbance in blank wells.

ANCA levels may be determined relative to a standard consisting of pooled sera obtained from well-characterized pANCA-positive patients. Results are expressed as ELISA units. Sera with circulating ANCA levels exceeding the reference range value may also be termed ANCA positive, whereas numerical values that are below the reference range may also be termed ANCA negative.

Example 4. Determination of the Presence of pANCA

This example illustrates an analysis of the presence or absence of pANCA in a sample using an immunofluorescence assay as described, e.g., in U.S. Pat. Nos. 5,750,355 and 5,830,675. In particular, the presence of pANCA is detected by assaying for the loss of a positive value (e.g., loss of a detectable antibody marker and/or a specific cellular staining pattern as compared to a control) upon treatment of neutrophils with DNase.

Neutrophils isolated from a sample such as serum are immobilized on a glass side according to the following protocol:
1. Resuspend neutrophils in a sufficient volume of 1× Hanks' Balanced Salt Solution (HBSS) to achieve about $2.5 \times 10^6$ cells per ml.
2. Use a Cytospin3 centrifuge (Shandon, Inc.; Pittsburgh, Pa.) at 500 rpm for 5 minutes to apply 0.01 ml of the resuspended neutrophils to each slide.
3. Fix neutrophils to slide by incubating slides for 10 minutes in sufficient volume of 100% methanol to cover sample. Allow to air dry. The slides may be stored at −20° C.

The immobilized, fixed neutrophils are then treated with DNase as follows:
1. Prepare a DNase solution by combining 3 units of Promega RQ1™ DNase (Promega; Madison, Wis.) per ml buffer containing 40 mM of TRIS-HCl (pH 7.9), 10 mM of sodium chloride, 6 mM magnesium chloride, and 10 mM calcium chloride.
2. Rinse slides prepared using the above protocol with about 100 ml phosphate buffered saline (pH 7.0-7.4) for 5 minutes. Incubate immobilized neutrophils in 0.05 ml of DNase solution per slide for about 30 minutes at 37° C. Wash the slides three times with about 100-250 ml phosphate buffered saline at room temperature. The DNase reaction carried out as described herein causes substantially complete digestion of cellular DNA without significantly altering nuclear or cellular neutrophil morphology.

Next, an immunofluorescence assay is performed on the DNase-treated, fixed neutrophils according to the following protocol:
1. Add 0.05 ml of a 1:20 dilution of human sera in phosphate buffered saline to slides treated with DNase and to untreated slides. Add 0.05 ml phosphate buffered saline to clean slides as blanks. Incubate for about 0.5 to 1.0 hour at room temperature in sufficient humidity to minimize volume loss.
2. Rinse off sera by dipping into a container having 100-250 ml phosphate buffered saline.

3. Soak slide in phosphate buffered saline for 5 minutes. Blot lightly.
4. Add 0.05 ml goat F(ab')$_2$ anti-human IgG(μ)-FITC (Tago Immunologicals; Burlingame, Calif.), at a 1:1000 antibody:phosphate buffered saline dilution, to each slide. Incubate for 30 minutes at room temperature in sufficient humidity to minimize volume loss.
5. Rinse off antibody with 100-250 ml phosphate buffered saline. Soak slides for 5 minutes in 100-250 ml phosphate buffered saline, then allow to air dry.
6. Read fluorescence pattern on fluorescence microscope at 40×.
7. If desired, any DNA can be stained with propidium iodide stain by rinsing slides well with phosphate buffered saline at room temperature and stain for 10 seconds at room temperature. Wash slide three times with 100-250 ml phosphate buffered saline at room temperature and mount cover slip.

The immunofluorescence assay described above can be used to determine the presence of pANCA in DNase-treated, fixed neutrophils, e.g., by the presence of a pANCA reaction in control neutrophils (i.e., fixed neutrophils that have not been DNase-treated) that is abolished upon DNase treatment or by the presence of a pANCA reaction in control neutrophils that becomes cytoplasmic upon DNase treatment.

Example 5. Predictive Value of the Markers

This example illustrates the stability of serological markers and their predictive value before and after right hemicolectomy with ileocolonic anastomosis in patients with Crohn's disease.

Background:

Preventing postoperative endoscopic (ER) and clinical recurrence (CR) remains a challenging issue in patients with Crohn's disease (CD) undergoing an intestinal resection. As detailed above, a risk panel of pre-operative clinical and serological markers (e.g., smoking behavior, Fla2, and pANCA) can guide postoperative prophylactic therapy. In this example, it is demonstrated that serological markers can be used to evaluate the post-operative association with both ER and CR.

Methods:

The study population consisted of 71 consecutive patients (33 males, 20 active smokers, median age 42.7 years) undergoing an ileal resection with ileocolonic anastomosis for refractory CD, in whom a serum sample was collected both ≤1 week prior to surgery and 6 months thereafter. All patients were followed prospectively and underwent a post-operative endoscopic evaluation at 6 months. Postoperative ER was defined as an endoscopic recurrence score of i3 or i4. Sera were for the expression of anti-*Saccharomyces cerevisiae* IgA and IgG antibodies, three different anti-flagellin antibodies (CBir1, Fla2 and FlaX), antibodies to the outer-membrane porin C of *Escherichia coli* (OmpC), and atypical perinuclear antineutrophilic cytoplasmic antibodies (pANCA). The Q3 value of each individual marker was defined as the cut-off point.

Results:

At month 6, ER and CR were observed in 20 (28%) and 12 (17%) patients, respectively. During a median (IQR) follow-up of 26.8 (18.1-39.2) months, 24 (34%) of patients developed CR. As shown in Table 1, a significant decrease of ASCA IgA and IgG, CBir1 and FlaX was demonstrated post-operatively, while a significant increase was noted for OmpC. The absolute and relative post-operative changes of these markers were not associated with ER or CR. However, active smoking, ASCA IgA>72 EU, OmpC>23 EU and positive pANCA at month 6 were associated with ER. In multivariate analysis, OmpC>23 EU was associated with ER [Odds ratio 4.398 (1.379-14.028), p=0.012]. In 59 patients without CR at month 6, previous intestinal resection, ER, Fla2>56 EU, FlaX>74 EU, and positive pANCA at month 6 were predictive of clinical recurrence. In Cox regression multivariate analysis, both ER [7.926 (2.256-27.848), p=0.001] and positive pANCA [4.741 (1.378-16.313), p=0.014] were independent predictors of long-term CR.

Conclusions:

This example demonstrates a clear evolution of serological markers in the postoperative phase. This observation reflects a changing microbial environment. Six months after right hemicolectomy, OmpC antibodies were independently associated with postoperative ER. Interestingly, not only ER but also presence of pANCA at month 6 was an independent predictor of long-term CR.

| Marker | Pre-operative, median (IQR) | Post-operative, median (IQR) | Wilcoxon signed rank p-value |
|---|---|---|---|
| ASCA IgA | 34.05 (9.56-89.34) | 21.39 (11.59-73.18) | p < 0.001 |
| ASCA IgG | 29.07 (11.10-63.86) | 25.22 (12.00-35.91) | p < 0.001 |
| CBir1 | 30.31 (16.78-89.28) | 24.91 (16.37-49.60) | p < 0.001 |
| Fla2 | 31.01 (16.04-66.79) | 42.54 (19.61-55.95) | p = 0.363 |
| FlaX | 52.49 (25.63-95.80) | 51.47 (23.49-73.87) | p = 0.001 |
| OmpC | 6.58 (2.63-13.17) | 12.66 (9.29-22.38) | p < 0.001 |

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

VI. Informal Sequence Listing

```
<210>SEQ ID NO 1
<211>LENGTH: 460
<212>TYPE: PRT
<213>ORGANISM: Artificial Sequence
<220>FEATURE:
<223>OTHER INFORMATION: A4-Fla2, also known as Flat = Synthetic Construct
<400>SEQUENCE: 1
```

```
Met Val Val Gln His Asn Leu Arg Ala Met Asn Ser Asn Arg Met Leu
 1               5                  10                  15
```

-continued

```
Gly Ile Thr Gln Gly Ser Leu Asn Lys Ser Thr Glu Lys Leu Ser Ser
            20                  25                  30

Gly Tyr Lys Val Asn Arg Ala Ala Asp Asp Ala Ala Gly Leu Ser Ile
        35                  40                  45

Ser Glu Lys Met Arg Lys Gln Ile Arg Gly Leu Ser Gln Ala Ser Leu
 50                  55                  60

Asn Ala Glu Asp Gly Ile Ser Ala Val Gln Thr Ala Glu Gly Ala Leu
 65                  70                  75                  80

Thr Glu Val His Asp Met Leu Gln Arg Met Asn Glu Leu Ala Val Lys
                85                  90                  95

Ala Ala Asn Gly Thr Asn Ser Thr Ser Asp Arg Gln Thr Ile Gln Asp
            100                 105                 110

Glu Val Asp Gln Leu Leu Thr Glu Ile Asp Arg Val Ala Glu Thr Thr
        115                 120                 125

Lys Phe Asn Glu Leu Tyr Thr Leu Lys Gly Asp Glu Asp Lys Val Thr
    130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Gln Lys
            180                 185                 190

Gln Gln Gly Glu Ile Ile Thr Ser Ser Val Lys Ile Gly Gln Gln Val
        195                 200                 205

Thr Ile Asp Gly Ile Met Tyr Thr Cys Thr Ala Thr Val Ser Asn Ala
    210                 215                 220

Asp Lys Phe Glu Leu Thr Lys Asp Asp Leu Ile Ala Lys Leu Asp Thr
225                 230                 235                 240

Ser Ser Leu Ser Ile Met Ser Val Asn Gly Lys Thr Tyr Tyr Gly Ala
                245                 250                 255

Gly Ile Thr Asp Asp Arg Thr Val Val Ser Ser Ile Gly Ala Tyr Lys
            260                 265                 270

Leu Ile Gln Lys Glu Leu Gly Leu Ala Ser Ser Ile Gly Ala Asp Gly
        275                 280                 285

Ser Thr Gln Ala Ser Val Asn Ala Gly Val Asp Gly Lys Thr Leu Lys
    290                 295                 300

Lys Pro Ser Phe Glu Gly Lys Trp Val Phe Ser Ile Asp Lys Gly Ser
305                 310                 315                 320

Val Gln Val Arg Glu Asp Ile Asp Phe Ser Leu His Val Gly Ala Asp
                325                 330                 335

Ala Asp Met Asn Asn Lys Ile Ala Val Lys Ile Gly Ala Leu Asp Thr
            340                 345                 350

Lys Gly Leu Gly Ile Gln Gly Leu Asn Val Lys Asp Thr Thr Gly Ala
        355                 360                 365

Ala Ala Thr Tyr Ala Ile Asp Ser Ile Ala Asp Ala Val Ala Arg Ile
    370                 375                 380

Ser Ala Gln Arg Ser Leu Leu Gly Ala Val Gln Asn Arg Leu Glu His
385                 390                 395                 400

Thr Ile Asn Asn Leu Asp Asn Val Val Glu Asn Thr Thr Ala Ala Glu
                405                 410                 415

Ser Gln Ile Arg Asp Thr Asp Met Ala Thr Glu Met Val Lys Tyr Ser
            420                 425                 430

Asn Asn Asn Val Leu Ala Gln Ala Gly Gln Ser Met Leu Ala Gln Ser
        435                 440                 445
```

-continued

```
        Asn Gln Ala Asn Gln Gly Val Leu Ser Leu Leu Gly
        450                 455                 460
```

<210> SEQ ID NO 2
<211> LENGTH: 493
<212> TYPE: PRT
<213> ORGANISM: Unknown
<220> FEATURE:
<223> OTHER INFORMATION: Description of Unknown Sequence: full-length CBir-1
      flagellin
      from C3H/HeJ Bir mouse cecal bacteria genomic DNA random shear
      expression library PCR amplification

<400> SEQUENCE: 2

```
        Met Val Val Gln His Asn Leu Gln Ala Met Asn Ser Asn Arg Met Leu
                        5                   10                  15

Gly Ile Thr Gln Lys Thr Ala Ser Lys Ser Thr Glu Lys Leu Ser Ser
                        20                  25                  30

Gly Tyr Ala Ile Asn Arg Ala Ala Asp Asn Ala Ala Gly Leu Ala Ile
                        35                  40                  45

Ser Glu Lys Met Arg Lys Gln Ile Arg Gly Leu Thr Gln Ala Ser Thr
                50                  55                  60

Asn Ala Glu Asp Gly Ile Ser Ser Val Gln Thr Ala Glu Gly Ala Leu
        65                  70                  75                  80

Thr Glu Val His Asp Met Leu Gln Arg Met Asn Glu Leu Ala Ile Gln
                        85                  90                  95

Ala Ala Asn Gly Thr Asn Ser Glu Asp Asp Arg Ser Tyr Ile Gln Asp
                        100                 105                 110

Glu Ile Asp Gln Leu Thr Gln Glu Ile Asp Arg Val Ala Glu Thr Thr
                        115                 120                 125

Lys Phe Asn Glu Thr Tyr Leu Leu Lys Gly Asp Thr Lys Asn Val Asp
                        130                 135                 140

Ala Met Asp Tyr Thr Tyr Ser Tyr Lys Ala Val Thr Thr Asn Thr Val
        145                 150                 155                 160

Ala Arg Ala Ser Val Leu Ala Ala Glu Asn Thr Ala Thr Gly Met Ser
                        165                 170                 175

Val Ser Ile Ser Phe Ala Ala Asn Ser Gly Lys Val Thr Ala Ala Asp
                        180                 185                 190

Ser Asn Asn Leu Ala Lys Ala Ile Arg Asp Gln Gly Phe Thr Ile Thr
                        195                 200                 205

Thr Ser Thr Gln Asn Gly Lys Val Val Tyr Gly Leu Glu Leu Asn Gly
                        210                 215                 220

Ser Asp Ala Lys Ala Asn Tyr Thr Val Ser Thr Val Ser Met Glu Ala
        225                 230                 235                 240

Gly Thr Phe Lys Ile Leu Asn Ser Asn Lys Gln Val Val Ala Ser Val
                        245                 250                 255

Thr Ile Ser Thr Thr Ala Ser Phe Lys Lys Val Ser Gly Met Ser Gln
                        260                 265                 270

Ile Val Thr Ala Tyr Ser Val Ser Ala Ala Tyr Ala Thr Gly Asp Val
                        275                 280                 285

Tyr Ser Leu Tyr Asp Ala Asp Gly Asn Ala Ile Ser Ala Asn Lys Leu
                        290                 295                 300

Asp Lys Tyr Phe Thr Ala Gly Gly Ala Thr Glu Ala Gly Gly Ile Ala
        305                 310                 315                 320

Thr Thr Leu Ser Ala Asn Ser Gly Val Pro Lys Val Tyr Asp Val Leu
                        325                 330                 335

Gly Lys Glu Val Ser Ala Val Ser Ile Ala Ser Thr Leu Val Thr Ala
                        340                 345                 350
```

-continued

```
        Val Lys Asp Lys Thr Ala Ala Leu Lys Met Asn Phe His Val Gly Ala
                    355                 360                 365

Asp Gly Thr Asp Asn Asn Lys Ile Lys Ile Asn Ile Glu Ala Met Thr
        370                 375                 380

Ala Lys Ser Leu Gly Val Asn Gly Leu Lys Val Ser Gly Ser Ser Gly
        385                 390                 395                 400

Thr Asn Ala Thr Asn Ala Ile Glu Ile Ile Ala Gly Ala Ile Lys Lys
                        405                 410                 415

Val Ser Thr Gln Arg Ser Ala Leu Gly Ala Val Gln Asn Arg Leu Glu
                    420                 425                 430

His Thr Ile Asn Asn Leu Asp Asn Ile Val Glu Asn Thr Thr Ala Ala
                435                 440                 445

Glu Ser Gly Ile Arg Asp Thr Asp Met Ala Thr Glu Met Val Lys Tyr
            450                 455                 460

Ser Asn Ala Asn Ile Leu Ser Gln Ala Gly Gln Ser Met Leu Ala Gln
        465                 470                 475                 480

Ser Asn Gln Ser Asn Gln Gly Val Leu Gln Leu Gln
                        485                 490
```

<210> SEQ ID NO 3
<211> LENGTH: 458
<212> TYPE: PRT
<213> ORGANISM: Unknown
<220> FEATURE:
<223> OTHER INFORMATION: Description of Unknown Sequence: full-length
Flagellin X
from C3H/HeJ Bir mouse cecal bacteria genomic DNA random shear
expression library PCR amplification

<400> SEQUENCE: 3

```
        Met Val Val Gln His Asn Leu Arg Ala Met Asn Ser Asn Arg Met Leu Gly
                        5                   10                  15

Ile Thr Gln Gly Ser Leu Asn Lys Ser Thr Glu Lys Leu Ser Ser Gly
                    20                  25                  30

Tyr Lys Val Asn Arg Ala Ala Asp Asp Ala Ala Gly Leu Ser Ile Ser
                35                  40                  45

Glu Lys Met Arg Lys Gln Ile Arg Gly Leu Ser Gln Ala Ser Leu Asn
        50                  55                  60                  65

Ala Glu Asp Gly Ile Ser Ala Val Gln Thr Ala Glu Gly Ala Leu Thr
                        70                  75                  80

Glu Val His Asp Met Leu Gln Arg Met Asn Glu Leu Ala Val Lys Ala
                    85                  90                  95

Ala Asn Gly Thr Asn Ser Thr Ser Asp Arg Gln Thr Ile Gln Asp Glu
                100                 105                 110

Val Asp Gln Leu Leu Thr Glu Ile Asp Arg Val Ala Glu Thr Thr Lys
        115                 120                 125

Phe Asn Glu Leu Tyr Thr Leu Lys Gly Asp Glu Asp Lys Val Thr Arg
        130                 135                 140                 145

Tyr Leu Ser Ala His Asp Ala Gly Ile Glu Gly Thr Leu Thr Gln Gly
                        150                 155                 160

Ala Thr Asn Ala Thr Phe Ser Met Asp Gln Leu Lys Phe Gly Asp Thr
                    165                 170                 175

Ile Met Ile Ala Gly Arg Glu Tyr His Ile Ser Gly Thr Lys Ala Glu
                180                 185                 190

Gln Ala Ala Ile Ile Thr Ala Ser Val Lys Ile Gly Gln Gln Val Thr
            195                 200                 205

Ile Asp Gly Ile Met Tyr Thr Cys Ser Ser Val Ser Asn Ala Asp Lys
        210                 215                 220                 225

Phe Glu Leu Lys Ser Glu Asp Leu Ile Ala Lys Leu Asp Thr Ser Ser
```

-continued

```
            230                 235                 240
Leu Ser Ile Met Ser Val Asn Gly Lys Thr Tyr Tyr Gly Ala Gly Ile
                245                 250                 255
Thr Asp Asp Arg Thr Val Val Ser Ser Ile Gly Ala Tyr Lys Leu Ile
            260                 265                 270
Gln Lys Glu Leu Gly Leu Ala Ser Ser Ile Gly Ala Asp Gly Ala Thr
        275                 280                 285
Gln Ala Ser Val Asn Ala Gly Val Asp Gly Lys Thr Leu Met Lys Pro
290                 295                 300                 305
Ser Phe Glu Gly Lys Trp Val Phe Ser Ile Asp Lys Gly Ser Val Gln
                310                 315                 320
Val Arg Glu Asp Ile Asp Phe Ser Leu His Val Gly Ala Asp Ala Asp
            325                 330                 335
Met Asn Asn Lys Ile Ala Val Lys Ile Gly Ala Leu Asp Thr Lys Gly
            340                 345                 350
Leu Gly Ile Gln Gly Leu Asn Val Lys Asp Thr Thr Gly Ala Ala Ala
        355                 360                 365
Thr Tyr Ala Ile Asp Ser Ile Ala Asp Ala Val Ala Arg Ile Ser Ala
370                 375                 380                 385
Gln Arg Ser Leu Leu Gly Ala Val Gln Asn Arg Leu Glu His Thr Ile
                390                 395                 400
Asn Asn Leu Asp Asn Val Val Glu Asn Thr Thr Ala Ala Glu Ser Gln
            405                 410                 415
Ile Arg Asp Thr Asp Met Ala Thr Glu Met Val Lys Tyr Ser Asn Asn
            420                 425                 430
Asn Val Leu Ala Gln Ala Gly Gln Ser Met Leu Ala Gln Ser Asn Gln
        435                 440                 445
Ala Asn Gln Gly Val Leu Gln Leu Leu Gln
450                 455
```

SEQUENCE LISTING

<160> NUMBER OF SEQ ID NOS: 3

<210> SEQ ID NO 1
<211> LENGTH: 460
<212> TYPE: PRT
<213> ORGANISM: Artificial Sequence
<220> FEATURE:
<223> OTHER INFORMATION: A4-Fla2, also known as Fla2=Synthetic Construct

<400> SEQUENCE: 1

```
Met Val Val Gln His Asn Leu Arg Ala Met Asn Ser Asn Arg Met Leu
1               5                   10                  15
Gly Ile Thr Gln Gly Ser Leu Asn Lys Ser Thr Glu Lys Leu Ser Ser
            20                  25                  30
Gly Tyr Lys Val Asn Arg Ala Ala Asp Asp Ala Ala Gly Leu Ser Ile
        35                  40                  45
Ser Glu Lys Met Arg Lys Gln Ile Arg Gly Leu Ser Gln Ala Ser Leu
    50                  55                  60
Asn Ala Glu Asp Gly Ile Ser Ala Val Gln Thr Ala Glu Gly Ala Leu
65                  70                  75                  80
Thr Glu Val His Asp Met Leu Gln Arg Met Asn Glu Leu Ala Val Lys
                85                  90                  95
Ala Ala Asn Gly Thr Asn Ser Ser Asp Arg Gln Thr Ile Gln Asp
            100                 105                 110
```

Glu Val Asp Gln Leu Leu Thr Glu Ile Asp Arg Val Ala Glu Thr Thr
            115                 120                 125

Lys Phe Asn Glu Leu Tyr Thr Leu Lys Gly Asp Glu Asp Lys Val Thr
        130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Gln Lys
            180                 185                 190

Gln Gln Gly Glu Ile Ile Thr Ser Ser Val Lys Ile Gly Gln Gln Val
        195                 200                 205

Thr Ile Asp Gly Ile Met Tyr Thr Cys Thr Ala Thr Val Ser Asn Ala
210                 215                 220

Asp Lys Phe Glu Leu Thr Lys Asp Asp Leu Ile Ala Lys Leu Asp Thr
225                 230                 235                 240

Ser Ser Leu Ser Ile Met Ser Val Asn Gly Lys Thr Tyr Tyr Gly Ala
                245                 250                 255

Gly Ile Thr Asp Asp Arg Thr Val Val Ser Ser Ile Gly Ala Tyr Lys
            260                 265                 270

Leu Ile Gln Lys Glu Leu Gly Leu Ala Ser Ser Ile Gly Ala Asp Gly
        275                 280                 285

Ser Thr Gln Ala Ser Val Asn Ala Gly Val Asp Gly Lys Thr Leu Lys
290                 295                 300

Lys Pro Ser Phe Glu Gly Lys Trp Val Phe Ser Ile Asp Lys Gly Ser
305                 310                 315                 320

Val Gln Val Arg Glu Asp Ile Asp Phe Ser Leu His Val Gly Ala Asp
                325                 330                 335

Ala Asp Met Asn Asn Lys Ile Ala Val Lys Ile Gly Ala Leu Asp Thr
            340                 345                 350

Lys Gly Leu Gly Ile Gln Gly Leu Asn Val Lys Asp Thr Thr Gly Ala
        355                 360                 365

Ala Ala Thr Tyr Ala Ile Asp Ser Ile Ala Asp Ala Val Ala Arg Ile
370                 375                 380

Ser Ala Gln Arg Ser Leu Leu Gly Ala Val Gln Asn Arg Leu Glu His
385                 390                 395                 400

Thr Ile Asn Asn Leu Asp Asn Val Val Glu Asn Thr Thr Ala Ala Glu
                405                 410                 415

Ser Gln Ile Arg Asp Thr Asp Met Ala Thr Glu Met Val Lys Tyr Ser
            420                 425                 430

Asn Asn Asn Val Leu Ala Gln Ala Gly Gln Ser Met Leu Ala Gln Ser
        435                 440                 445

Asn Gln Ala Asn Gln Gly Val Leu Ser Leu Leu Gly
450                 455                 460

<210> SEQ ID NO 2
<211> LENGTH: 493
<212> TYPE: PRT
<213> ORGANISM: Unknown
<220> FEATURE:
<223> OTHER INFORMATION: Description of Unknown Sequence:full-length
      CBir-1 flagellin from C3H/HeJ Bir mouse cecal bacteria genomic DNA
      random shear expression library PCR amplification

<400> SEQUENCE: 2

```
Met Val Val Gln His Asn Leu Gln Ala Met Asn Ser Asn Arg Met Leu
 1               5                  10                  15

Gly Ile Thr Gln Lys Thr Ala Ser Lys Ser Thr Glu Lys Leu Ser Ser
             20                  25                  30

Gly Tyr Ala Ile Asn Arg Ala Ala Asp Asn Ala Ala Gly Leu Ala Ile
             35                  40                  45

Ser Glu Lys Met Arg Lys Gln Ile Arg Gly Leu Thr Gln Ala Ser Thr
 50                  55                  60

Asn Ala Glu Asp Gly Ile Ser Ser Val Gln Thr Ala Glu Gly Ala Leu
 65                  70                  75                  80

Thr Glu Val His Asp Met Leu Gln Arg Met Asn Glu Leu Ala Ile Gln
                 85                  90                  95

Ala Ala Asn Gly Thr Asn Ser Glu Asp Asp Arg Ser Tyr Ile Gln Asp
             100                 105                 110

Glu Ile Asp Gln Leu Thr Gln Glu Ile Asp Arg Val Ala Glu Thr Thr
             115                 120                 125

Lys Phe Asn Glu Thr Tyr Leu Leu Lys Gly Asp Thr Lys Asn Val Asp
 130                 135                 140

Ala Met Asp Tyr Thr Tyr Ser Tyr Lys Ala Val Thr Thr Asn Thr Val
145                 150                 155                 160

Ala Arg Ala Ser Val Leu Ala Ala Glu Asn Thr Ala Thr Gly Met Ser
                 165                 170                 175

Val Ser Ile Ser Phe Ala Ala Asn Ser Gly Lys Val Thr Ala Ala Asp
             180                 185                 190

Ser Asn Asn Leu Ala Lys Ala Ile Arg Asp Gln Gly Phe Thr Ile Thr
             195                 200                 205

Thr Ser Thr Gln Asn Gly Lys Val Val Tyr Gly Leu Glu Leu Asn Gly
 210                 215                 220

Ser Asp Ala Lys Ala Asn Tyr Thr Val Ser Thr Val Ser Met Glu Ala
225                 230                 235                 240

Gly Thr Phe Lys Ile Leu Asn Ser Asn Lys Gln Val Val Ala Ser Val
                 245                 250                 255

Thr Ile Ser Thr Thr Ala Ser Phe Lys Lys Val Ser Gly Met Ser Gln
             260                 265                 270

Ile Val Thr Ala Tyr Ser Val Ser Ala Ala Tyr Ala Thr Gly Asp Val
             275                 280                 285

Tyr Ser Leu Tyr Asp Ala Asp Gly Asn Ala Ile Ser Ala Asn Lys Leu
 290                 295                 300

Asp Lys Tyr Phe Thr Ala Gly Gly Ala Thr Glu Ala Gly Gly Ile Ala
305                 310                 315                 320

Thr Thr Leu Ser Ala Asn Ser Gly Val Pro Lys Val Tyr Asp Val Leu
                 325                 330                 335

Gly Lys Glu Val Ser Ala Val Ser Ile Ala Ser Thr Leu Val Thr Ala
             340                 345                 350

Val Lys Asp Lys Thr Ala Ala Leu Lys Met Asn Phe His Val Gly Ala
             355                 360                 365

Asp Gly Thr Asp Asn Asn Lys Ile Lys Ile Asn Ile Glu Ala Met Thr
 370                 375                 380

Ala Lys Ser Leu Gly Val Asn Gly Leu Lys Ser Gly Ser Ser Gly
385                 390                 395                 400

Thr Asn Ala Thr Asn Ala Ile Glu Ile Ile Ala Gly Ala Ile Lys Lys
                 405                 410                 415

Val Ser Thr Gln Arg Ser Ala Leu Gly Ala Val Gln Asn Arg Leu Glu
```

```
                       420                 425                 430

His Thr Ile Asn Asn Leu Asp Asn Ile Val Glu Asn Thr Thr Ala Ala
                435                 440                 445

Glu Ser Gly Ile Arg Asp Thr Asp Met Ala Thr Glu Met Val Lys Tyr
            450                 455                 460

Ser Asn Ala Asn Ile Leu Ser Gln Ala Gly Gln Ser Met Leu Ala Gln
465                 470                 475                 480

Ser Asn Gln Ser Asn Gln Gly Val Leu Gln Leu Leu Gln
                485                 490

<210> SEQ ID NO 3
<211> LENGTH: 459
<212> TYPE: PRT
<213> ORGANISM: Unknown
<220> FEATURE:
<223> OTHER INFORMATION: Description of Unknown Sequence:full-length
      Flagellin X from C3H/HeJ Bir mouse cecal bacteria genomic DNA
      random shear expression library PCR amplification

<400> SEQUENCE: 3

Met Val Val Gln His Asn Leu Arg Ala Met Asn Ser Asn Arg Met Leu
1               5                   10                  15

Gly Ile Thr Gln Gly Ser Leu Asn Lys Ser Thr Glu Lys Leu Ser Ser
                20                  25                  30

Gly Tyr Lys Val Asn Arg Ala Ala Asp Asp Ala Ala Gly Leu Ser Ile
            35                  40                  45

Ser Glu Lys Met Arg Lys Gln Ile Arg Gly Leu Ser Gln Ala Ser Leu
        50                  55                  60

Asn Ala Glu Asp Gly Ile Ser Ala Val Gln Thr Ala Glu Gly Ala Leu
65                  70                  75                  80

Thr Glu Val His Asp Met Leu Gln Arg Met Asn Glu Leu Ala Val Lys
                85                  90                  95

Ala Ala Asn Gly Thr Asn Ser Thr Ser Asp Arg Gln Thr Ile Gln Asp
                100                 105                 110

Glu Val Asp Gln Leu Leu Thr Glu Ile Asp Arg Val Ala Glu Thr Thr
            115                 120                 125

Lys Phe Asn Glu Leu Tyr Thr Leu Lys Gly Asp Glu Asp Lys Val Thr
        130                 135                 140

Arg Tyr Leu Ser Ala His Asp Ala Gly Ile Glu Gly Thr Leu Thr Gln
145                 150                 155                 160

Gly Ala Thr Asn Ala Thr Phe Ser Met Asp Gln Leu Lys Phe Gly Asp
                165                 170                 175

Thr Ile Met Ile Ala Gly Arg Glu Tyr His Ile Ser Gly Thr Lys Ala
            180                 185                 190

Glu Gln Ala Ala Ile Ile Thr Ala Ser Val Lys Ile Gly Gln Gln Val
        195                 200                 205

Thr Ile Asp Gly Ile Met Tyr Thr Cys Ser Ser Val Ser Asn Ala Asp
210                 215                 220

Lys Phe Glu Leu Lys Ser Glu Asp Leu Ile Ala Lys Leu Asp Thr Ser
225                 230                 235                 240

Ser Leu Ser Ile Met Ser Val Asn Gly Lys Thr Tyr Tyr Gly Ala Gly
                245                 250                 255

Ile Thr Asp Asp Arg Thr Val Val Ser Ser Ile Gly Ala Tyr Lys Leu
            260                 265                 270

Ile Gln Lys Glu Leu Gly Leu Ala Ser Ser Ile Gly Ala Asp Gly Ala
        275                 280                 285
```

-continued

```
Thr Gln Ala Ser Val Asn Ala Gly Val Asp Gly Lys Thr Leu Met Lys
    290                 295                 300

Pro Ser Phe Glu Gly Lys Trp Val Phe Ser Ile Asp Lys Gly Ser Val
305                 310                 315                 320

Gln Val Arg Glu Asp Ile Asp Phe Ser Leu His Val Gly Ala Asp Ala
                325                 330                 335

Asp Met Asn Asn Lys Ile Ala Val Lys Ile Gly Ala Leu Asp Thr Lys
                340                 345                 350

Gly Leu Gly Ile Gln Gly Leu Asn Val Lys Asp Thr Thr Gly Ala Ala
            355                 360                 365

Ala Thr Tyr Ala Ile Asp Ser Ile Ala Asp Ala Val Ala Arg Ile Ser
    370                 375                 380

Ala Gln Arg Ser Leu Leu Gly Ala Val Gln Asn Arg Leu Glu His Thr
385                 390                 395                 400

Ile Asn Asn Leu Asp Asn Val Val Glu Asn Thr Thr Ala Ala Glu Ser
                405                 410                 415

Gln Ile Arg Asp Thr Asp Met Ala Thr Glu Met Val Lys Tyr Ser Asn
                420                 425                 430

Asn Asn Val Leu Ala Gln Ala Gly Gln Ser Met Leu Ala Gln Ser Asn
                435                 440                 445

Gln Ala Asn Gln Gly Val Leu Gln Leu Leu Gln
    450                 455
```

What is claimed is:

1. A method for predicting post-operative recurrence of Crohn's disease (CD) in a subject with CD that is undergoing or planning on undergoing surgical treatment of the CD, the method comprising:
    (a) determining the presence of a first risk factor by detecting an elevated level of an anti-flagellin antibody in a pre-operative sample from the subject relative to a level of the anti-flagellin antibody from an average subject with CD;
    (b) determining the presence of a second risk factor by detecting the presence of perinuclear anti-neutrophilic cytoplasmic antibodies (pANCA) in the sample;
    (c) determining the presence of a third risk factor by determining whether the subject is an active smoker;
    (d) predicting a risk of post-operative recurrence of CD in the subject based upon the presence of the first, second, and third risk factors, wherein the recurrence of CD comprises endoscopic recurrence, histological recurrence, or clinical recurrence,
    wherein the presence of one risk factor is predictive of an increased risk of post-operative recurrence of CD relative to an average subject with CD undergoing surgical treatment of the CD, wherein the presence of two of the risk factors is predictive of a greater risk of post-operative recurrence of CD relative to the presence of one of the risk factors, and wherein the presence of three of the risk factors is predictive of greater risk of post-operative recurrence of CD relative to the presence of two of the risk factors; and
    (e) providing a post-operative CD therapy to the subject based on the presence of one two or three of the risk factors.

2. The method of claim 1, wherein the anti-flagellin antibody is selected from the group consisting of an anti-Fla2 antibody, an anti-FlaX antibody, and an anti-CBir1 antibody.

3. The method of claim 1, wherein the anti-flagellin antibody comprises an anti-Fla2 antibody.

4. The method of claim 1, wherein pANCA is positive.

5. The method of claim 1, wherein the elevated level of the anti-flagellin antibody comprises greater than 66 EU/ml of the anti-flagellin antibody.

6. The method of claim 1, wherein the post-operative recurrence comprises an endoscopic recurrence score of i3 or i4.

7. The method of claim 1, wherein the surgical treatment comprises an intestinal resection.

8. The method of claim 1, wherein the post-operative CD therapy comprises an additional surgical intervention.

9. The method of claim 1, wherein the post-operative CD therapy comprises a prophylactic drug treatment.

10. A method for predicting post-operative recurrence of CD in a subject with CD that is undergoing or planning on undergoing surgical treatment of the CD, the method comprising:
    (a) determining the presence of a first risk factor by detecting, by an immunoassay, a level of an anti-flagellin antibody greater than 66 EU/ml in a pre-operative sample from the subject;
    (b) determining the presence of a second risk factor by detecting the presence of pANCA in the sample; and
    (c) determining the presence of a third risk factor by determining whether the subject is an active smoker;
    (d) predicting a risk of post-operative recurrence of CD in the subject based upon the presence of the first, second, and third risk factors, wherein the recurrence of CD comprises endoscopic recurrence, histological recurrence, or clinical recurrence,
    wherein the presence of one risk factor is predictive of an increased risk of post-operative recurrence of CD relative to an average subject with CD undergoing surgical treatment of the CD, wherein the presence of two of the risk factors is predictive of a greater risk of post-operative recurrence of CD relative to the presence of one of the risk factors, and wherein the presence of three of the risk factors is predictive of greater risk of post-operative recurrence of CD relative to the presence of two of the risk factors.

11. The method of claim 10, further comprising: (e) providing a post-operative CD therapy to the subject based on the presence of one, two, or three of the risk factors.

12. The method of claim 10, wherein the post-operative recurrence comprises endoscopic recurrence.

13. The method of claim 10, wherein the surgical treatment comprises an intestinal resection.

14. The method of claim 10, wherein the anti-flagellin antibody comprises an anti-Fla2 antibody.

15. The method of claim 1, wherein the sample comprises a serum sample.

16. The method of claim 10, wherein the sample comprises a serum sample.

\* \* \* \* \*